(12) United States Patent
Pan et al.

(10) Patent No.: US 9,187,419 B2
(45) Date of Patent: Nov. 17, 2015

(54) INTERMEDIATES OF SITAGLIPTIN AND PREPARATION PROCESS THEREOF

(75) Inventors: Xianhua Pan, Taizhou (CN); Weijin Li, Taizhou (CN); Qunhui Zhang, Taizhou (CN); Libo Ruan, Taizhou (CN); Wansheng Yu, Taizhou (CN); Fei Deng, Taizhou (CN); Tianhua Ma, Taizhou (CN); Mingwang Huang, Taizhou (CN); Minhuan He, Taizhou (CN)

(73) Assignee: ZHEJIANG HISOAR PHARMACEUTICAL CO., LTD., Taizhou (CN)

( * ) Notice: Subject to any disclaimer, the term of this patent is extended or adjusted under 35 U.S.C. 154(b) by 48 days.

(21) Appl. No.: 13/988,261

(22) PCT Filed: Dec. 1, 2011

(86) PCT No.: PCT/CN2011/083315
§ 371 (c)(1),
(2), (4) Date: Jul. 10, 2013

(87) PCT Pub. No.: WO2012/072036
PCT Pub. Date: Jun. 7, 2012

(65) Prior Publication Data
US 2013/0281695 A1 Oct. 24, 2013

(30) Foreign Application Priority Data
Dec. 3, 2010 (CN) .......................... 2010 1 0579056

(51) Int. Cl.
*C07C 211/34* (2006.01)
*C07C 323/25* (2006.01)
*C07C 209/62* (2006.01)
*C07D 203/08* (2006.01)
*C07D 203/10* (2006.01)
*C07D 203/24* (2006.01)
*C07D 487/04* (2006.01)
*C07C 271/22* (2006.01)
*C07C 319/20* (2006.01)
*C07F 7/10* (2006.01)

(52) U.S. Cl.
CPC ............ *C07C 323/25* (2013.01); *C07C 209/62* (2013.01); *C07C 271/22* (2013.01); *C07C 319/20* (2013.01); *C07D 203/08* (2013.01); *C07D 203/10* (2013.01); *C07D 203/24* (2013.01); *C07D 487/04* (2013.01); *C07F 7/10* (2013.01)

(58) Field of Classification Search
CPC ..................................................... C07C 211/34
See application file for complete search history.

(56) References Cited

U.S. PATENT DOCUMENTS

2006/0069250 A1 * 3/2006 Deng et al. ..................... 540/450

FOREIGN PATENT DOCUMENTS

EP  0223440 A1 * 5/1987
WO  WO 2010031182 A1 * 3/2010

OTHER PUBLICATIONS

American Chemical Society (ACS). STN Chemical Abstract Service (CAS) RN Database. © 2013.*
Ooi, T., et al. "Pentacoordinate Orhanoaluminum Chemistry: Catalytic Efficiency of Me3Al in the Epoxide Cleavage Alkynyllithiums." Journal of the American Chemical Society. (1999), vol. 121, pp. 3328-3333.*
Bisai, A., et al. "An efficient approach to 2-substituted N-tosylpiperidines: Asymmetric synthesis of 2-(2-hydroxy substituted)—piperidine alkaloids." Tetrahedron Letters. (2007), vol. 48, pp. 1907-1910.*
Sureshkumar, D., et al. "Regio- and Stereospecific Synthesis of β-Sulfonamidodisulfides and β-Sulfonamidosulfides from Aziridines using Tetrathiomolybdate as a Sulfur Transfer Reagent." Journal of the American Chemical Society. (2007), vol. 72, pp. 2106-2117.*
Ganesh, V., et al. "Direct Synthesis of Functionalized Unsymmetrical β-Sulfonamido Disulfides by Tetrathiomolybdate Mediated Aziridine Ring-Opening Reactions." Journal of the American Chemical Society. (2009), vol. 74, pp. 7958-7961.*
Kim et al., "Triazolopiperazine-amides as dipeptidyl peptidase IV inhibitors: Close analogs of JANUVIA™ (sitagliptin phosphate)", Elsevier, Ltd., Bioorganic & Medicinal Chemistry Letters 17, pp. 3373-3377 (2007).
Kim et al., "(2R)-4-Oxo-4-[3-(Trifluoromethyl)-5,6-dihydro[1,2,4]triazolo[4,3-a]pyrazin-7(8H)-yl]-1-(2,4,5-trifluorophenyl) butan-2-amine: A Potent, Orally Active Dipeptidyl Peptidase IV Inhibitor for the Treatment of Type 2 Diabetes", American Chemical Society, J. Med. Chem, 48, pp. 141-151 (2005).

* cited by examiner

*Primary Examiner* — Andrew D Kosar
*Assistant Examiner* — John S Kenyon
(74) *Attorney, Agent, or Firm* — Westerman, Hattori, Daniels & Adrian, LLP

(57) ABSTRACT

Disclosed are intermediates of Sitagliptin, a preparation process thereof, and a process for synthesizing Sitagliptin using these intermediates. Sitagliptin is synthesized by using chiral amino compounds as a raw material, without having to build a chiral center with a chiral asymmetric catalytic hydrogenation, and high-pressure hydrogenation is avoided.

17 Claims, No Drawings

INTERMEDIATES OF SITAGLIPTIN AND PREPARATION PROCESS THEREOF

FIELD OF THE INVENTION

The present invention relates to the field of pharmaceutical synthesis. Specifically, the present invention relates to intermediates of Sitagliptin and a preparation process thereof, and a process for synthesizing Sitagliptin using these intermediates.

BACKGROUND OF THE INVENTION

Chiral amino-compound fragments widely exist in natural products and active molecules. It has long been a target encouraging the organic synthetic chemists to try to build chiral amino groups with high performance and selectivity. In 1979, Professor Kozikowski at University of Pittsburgh found that the organometallic reagents could selectively catalyze the ring-opening of aziridine compound to synthesize amino-compound (J. Org. Chem., 1979, 44, 788-2790). In recent years, the selective ring-opening of aziridine compound to synthesize amino-compound has been developed prosperously (Org. Lett., 2011, 3, 2349-2351). The synthesis methods of chiral amino compound from natural chiral sources are characterized by their simplicity and customizing the chiral structures or the like, and thus have definite advantages over the methods of chiral induction and chiral resolution.

Sitagliptin phosphate is the first dipeptidyl peptidase-IV ("DPP-IV") inhibitor for the treatment of type 2 diabetes mellitus which has been approved for marketing by the U.S. Food and Drug Administration (FDA) in 2006. Sitagliptin phosphate shows remarkable hypoglycemic activity whether it is used alone or in combination with metformin or pioglitazone. In addition, it is safe, well-tolerated, and with few adverse effects. Sitagliptin phosphate was developed by Merck & Co., Inc. under the tradename JANUVITA. It was approved by the Ministry of Health in Mexico on Aug. 8, 2006 for the treatment of type 2 diabetes mellitus by once daily medication, and was approved by FDA on Oct. 16, 2006 in US. By now, it has been approved by more than sixty countries around the world. It was reported that the third quarter earnings in 2007 was USD 0.185 billion and the value of sales till 2009 would be up to USD 1 billion. The maximum value of its sales is expected to be USD 1.4 billion after its successfully coming into the market. Therefore, Sitagliptin phosphate, as a hypoglycemic drug, is the latest international "blockbuster" product with extremely high added value. That means the development of this medicine is of great significance. However, by now, there is no enterprise which has the capacity of industrially producing Sitagliptin phosphate in China because of the high technical difficulties in the production. The disclosed synthetic routes of Sitagliptin phosphate are all designed by Merck & Co., Inc., which are reviewed as follows.

(1) U.S. Pat. No. 6,699,871 discloses a synthetic route of Sitagliptin, which is a synthesis method on gram scale suitable for R&D departments. In the method, the chiral source is used to induce a chiral alpha-amino acid compound which is then subjected to a diazotization reaction for forming beta-amino acid compound which can be used to build the required chiral center. The cost of raw materials required in this route is relatively high, and the operation of reaction is relatively complicated. Further, it is hard to control the technical process and the products' quality during the industrialization process. The synthetic route is as described below.

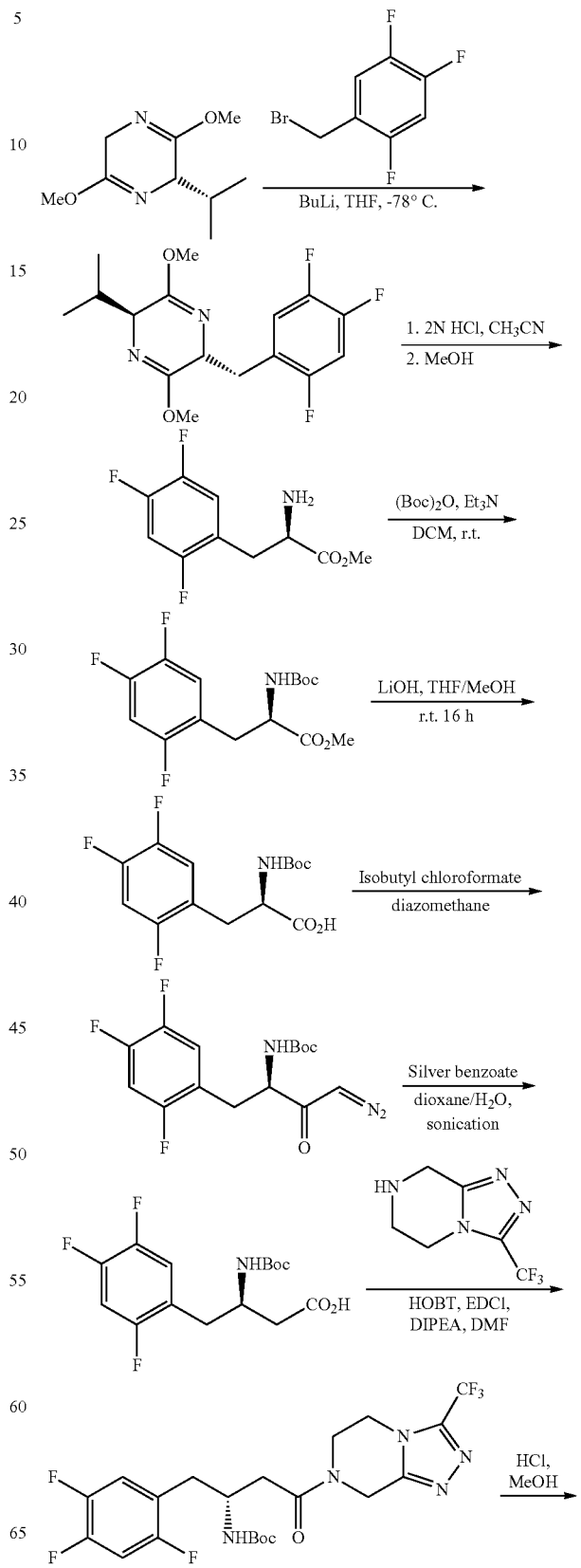

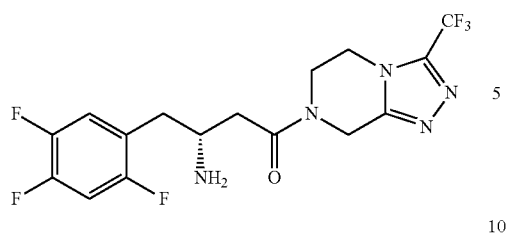
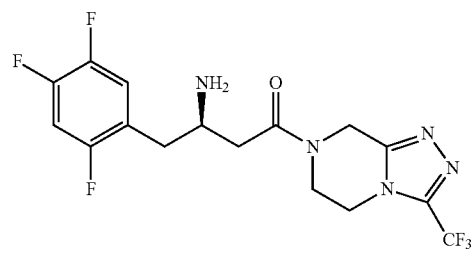

(2) WO 2004087650 discloses the second generation synthetic route of Sitagliptin developed by Merck & Co., Inc. In this method, a chiral phosphorus ruthenium catalyst is applied to the asymmetric catalytic hydrogenation of ketone to afford a chiral secondary alcohol which is then converted into a chiral secondary amine in order to obtain a chiral amine. However, in this route, Rh based catalyst is needed to be used in the key step of the asymmetric catalytic hydrogenation, thus the costs of this step is relatively high. In addition, during the industrialization, it is difficult to control the products' quality due to an apparent scaling effect when the reaction is performed in an amplified scale. The synthetic route is as described below.

(3) WO 2005003135 discloses the third generation synthetic method of Sitagliptin developed by Merck & Co., Inc. In this method S-phenylglycinamide is used as a chiral auxiliary for inducing catalytic hydrogenation to synthesize chiral amine. This route is relatively proper, however, the main problems of this method lie in that catalytic hydrogenations are needed twice and the Pt based catalyst used thereof is relatively expensive. Further, a large amount of Pd(OH)$_2$/C is used to remove the protective group in the final step, thereby rendering high cost. The synthetic route is as described below.

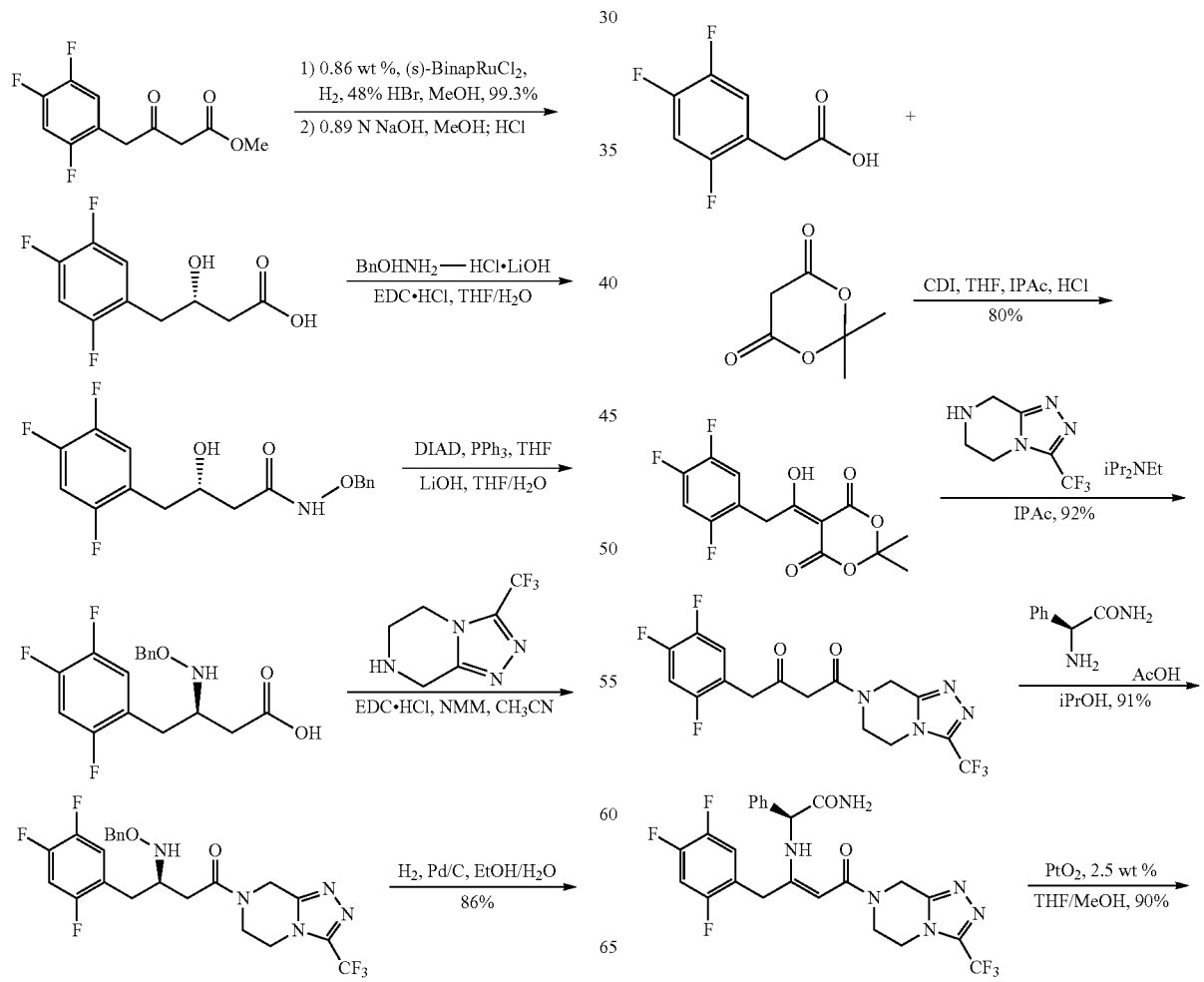

-continued

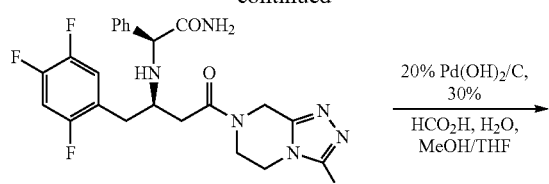

96% de

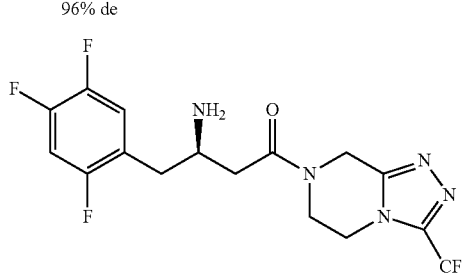

(4) WO 2007050485 discloses the latest synthetic method of Sitagliptin developed by Merck & Co., Inc. In this method, a chiral rhodium catalyst is applied to the asymmetric catalytic hydrogenation of enamine to build a chiral center. Due to fewer steps, this method is relatively simple. However, the expensive catalyst and chiral auxiliary are used in this method as well, and there still exists a scaling effect during the industrialization, which results in products of unstable quality. The synthetic route is as described below.

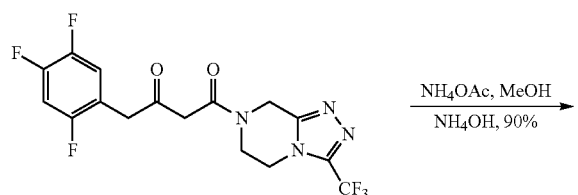

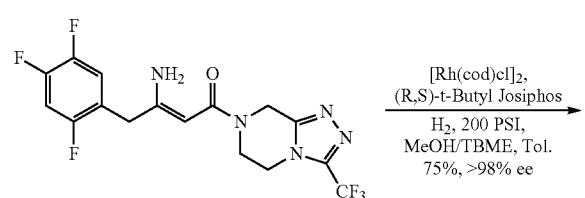

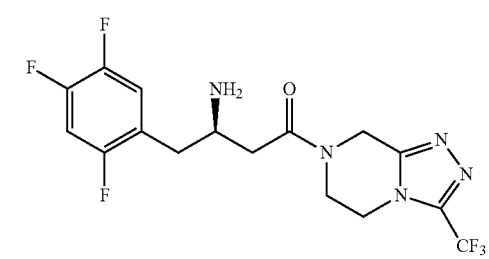

Owing to the shortcomings existing in the previous synthetic methods of Sitagliptin (i.e., low product yields, high costs, and not eco-friendly), a synthesis method with high yield, low cost and being eco-friendly would have a broad market prospect. Therefore, there is still a need of finding novel intermediates of Sitagliptin to develop new routes to improve the method for synthesizing Sitagliptin.

SUMMARY OF THE INVENTION

The present invention provides a new intermediate for synthesizing Sitagliptin, which is an aziridine compound of Formula I with absolute configuration R having the following structural formula:

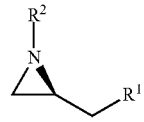

I wherein:
$R^1$ is —$CH_2SR^3$, wherein $R^3$ is $C_1$-$C_4$ alkyl; or $R^1$ is —$CH_2OR^4$, wherein $R^4$ is selected from the group consisting of hydrogen, methyl, substituted methyl, tetrahydropyranyl, methoxyphenyl, ethyl, benzyl, substituted benzyl and silyl;

wherein the substituted methyl is selected from the group consisting of methoxymethyl, methylthiomethyl, benzyloxymethyl, (p-methoxybenzyloxy)methyl, 2-methoxyethoxymethyl and 2-trimethylsilylethoxymethyl;

the substituted benzyl is selected from the group consisting of p-methoxybenzyl, 3,4-dimethoxybenzyl and p-nitrobenzyl;

the silyl is selected from the group consisting of trimethylsilyl, triethylsilyl, tri-isopropylsilyl, tert-butyldimethylsilyl, tert-butyldiphenylsilyl, diphenylmethylsilyl and tert-butylmethoxyphenylsilyl;

$R^2$ is selected from the group consisting of hydrogen, formate group, acyl, sulfonyl, benzyl and 4-methoxybenzyl;

wherein the formate group is selected from the group consisting of methoxycarbonyl, ethoxycarbonyl, 9-fluorenylmethoxycarbonyl, 2-chloro-3-indenylmethoxycarbonyl, 2,2,2-trichloroethoxycarbonyl, 2-trimethylsilylethoxycarbonyl, homobenzyloxycarbonyl, tert-butoxycarbonyl, benzyloxycarbonyl and allyloxycarbonyl;

the acyl is selected from the group consisting of formyl, acetyl, trifluoroacetyl and benzoyl;

the sulfonyl is benzenesulfonyl or trifluoromethylsulfonyl.

In the above-described aziridine compound of Formula I having absolute configuration R, it is further preferred that $R^1$ is —$CH_2SR^3$, wherein $R^3$ is methyl; or $R^1$ is —$CH_2OR^4$ and $R^4$ is selected from the group consisting of hydrogen, methoxymethyl, benzyl, p-nitrobenzyl, tert-butyldimethylsilyl and tert-butyldiphenylsilyl.

Preferably, $R^2$ is selected from the group consisting of formate group, acyl, sulfonyl, benzyl and 4-methoxybenzyl, wherein, the formate group is selected from the group consisting of methoxycarbonyl, tert-butoxycarbonyl, benzyloxycarbonyl and allyloxycarbonyl; the acyl is benzoyl; and the sulfonyl is benzenesulfonyl or trifluoromethylsulfonyl.

Further preferably, $R^1$ is —$CH_2SR^3$, wherein $R^3$ is methyl; or $R^1$ is —$CH_2OR^4$, wherein $R^4$ is selected from the group consisting of hydrogen, benzyl, and tert-butyldimethylsilyl; $R^2$ is selected from the group consisting of tert-butoxycarbonyl, benzyl, and benzenesulfonyl.

The present invention also provides a process for synthesizing the above-described aziridine compound of Formula I with absolute configuration R, which comprises the step of intramolecular cyclizing an amino-compound of Formula II with absolute configuration R in the presence of an alkali and a phase transfer catalyst to form an aziridine compound of Formula I with absolute configuration R;

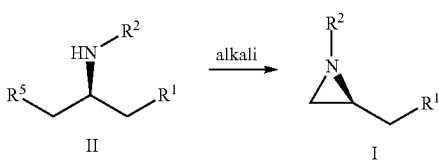

wherein:

$R^1$ is —$CH_2SR^3$, wherein $R^3$ is $C_1$-$C_4$ alkyl; or $R^1$ is —$CH_2OR^4$, wherein $R^4$ is selected from the group consisting of hydrogen, methyl, substituted methyl, tetrahydropyranyl, methoxyphenyl, ethyl, benzyl, substituted benzyl and silyl;

wherein the substituted methyl is selected from the group consisting of methoxymethyl, methylthiomethyl, benzyloxymethyl, (p-methoxybenzyloxy)methyl, 2-methoxyethoxymethyl and 2-trimethylsilylethoxymethyl;

the substituted benzyl is selected from the group consisting of p-methoxybenzyl, 3,4-dimethoxybenzyl and p-nitrobenzyl;

the silyl is selected from the group consisting of trimethylsilyl, triethylsilyl, tri-isopropylsilyl, tert-butyldimethylsilyl, tert-butyldiphenylsilyl, diphenylmethylsilyl and tert-butylmethoxyphenylsilyl;

$R^2$ is selected from the group consisting of hydrogen, formate group, acyl, sulfonyl, benzyl and 4-methoxybenzyl;

wherein the formate group is selected from the group consisting of methoxycarbonyl, ethoxycarbonyl, 9-fluorenylmethoxycarbonyl, 2-chloro-3-indenylmethoxycarbonyl, 2,2,2-trichloroethoxycarbonyl, 2-trimethylsilylethoxycarbonyl, homobenzyloxycarbonyl, tert-butoxycarbonyl, benzyloxycarbonyl and allyloxycarbonyl;

the acyl is selected from the group consisting of formyl, acetyl, trifluoroacetyl and benzoyl;

the sulfonyl is benzenesulfonyl or trifluoromethylsulfonyl;

$R^5$ is selected from the group consisting of hydroxyl, sulfonate, and halogen;

wherein the sulfonate is selected from the group consisting of methanesulfonate, p-toluenesulfonate and trifluoromethanesulfonate; the halogen is selected from the group consisting of chlorine, bromine and iodine.

Preferably, $R^1$ is —$CH_2SR^3$, wherein $R^3$ is methyl, or $R^1$ is —$CH_2OR^4$, wherein $R^4$ is selected from the group consisting of hydrogen, benzyl, and tert-butyldimethylsilyl; $R^2$ is selected from the group consisting of tert-butoxycarbonyl, benzyl, and benzenesulfonyl; $R^5$ is methanesulfonate or p-toluenesulfonate.

The alkali used herein includes organic alkali or inorganic alkali;

wherein the inorganic alkali is one or more alkalis selected from the group consisting of sodium hydroxide, potassium hydroxide, lithium hydride, sodium hydride, potassium hydride, calcium hydroxide, sodium carbonate, potassium phosphate and potassium carbonate;

the organic alkali is one or more alkalis selected from the group consisting of pyridine, substituted pyridine, piperidine, 1,8-diazabicyclo[5.4.0]undec-7-ene, $C_1$-$C_4$ aliphatic amine, $C_1$-$C_4$ sodium aliphatic alkoxide, $C_1$-$C_4$ potassium aliphatic alkoxide, butyl lithium, lithium diisopropylamide, lithium bis(trimethylsilyl)amide, sodium bis(trimethylsilyl)amide and potassium bis(trimethylsilyl)amide.

Preferably, the alkali is sodium hydride, sodium methoxide or the mixture thereof.

In the above-described synthesizing process, the solvent used in the reaction is an anhydrous solvent selected from the group consisting of tetrahydrofuran, methyltetrahydrofuran, diethyl ether, methyl tert-butyl ether, dimethylformamide, dimethyl acetamide, dimethyl sulfoxide and the like.

The present invention further provides a chiral amino compound of Formula IV with absolute configuration R, which has the following structural formula:

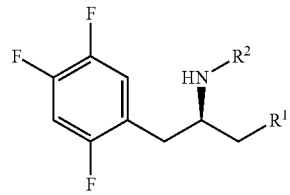

IV wherein:

$R^1$ is —$CH_2SR^3$, wherein $R^3$ is $C_1$-$C_4$ alkyl; or $R^1$ is —$CH_2OR^4$, wherein $R^4$ is selected from the group consisting of hydrogen, methyl, substituted methyl, tetrahydropyranyl, methoxyphenyl, ethyl, benzyl, substituted benzyl and silyl;

wherein, the substituted methyl is selected from the group consisting of methoxymethyl, methylthiomethyl, benzyloxymethyl, (p-methoxybenzyloxy)methyl, 2-methoxyethoxymethyl and 2-trimethylsilylethoxymethyl;

the substituted benzyl is selected from the group consisting of p-methoxybenzyl, 3,4-dimethoxybenzyl and p-nitrobenzyl;

the silyl is selected from the group consisting of trimethylsilyl, triethylsilyl, tri-isopropylsilyl, tert-butyldimethylsilyl, tert-butyldiphenylsilyl, diphenylmethylsilyl and tert-butylmethoxyphenylsilyl;

$R^2$ is selected from the group consisting of hydrogen, formate group, acyl, sulfonyl, benzyl and 4-methoxybenzyl;

wherein, the formate group is selected from the group consisting of methoxycarbonyl, ethoxycarbonyl, 9-fluorenylmethoxycarbonyl, 2-chloro-3-indenylmethoxycarbonyl, 2,2,2-trichloroethoxycarbonyl, 2-trimethylsilylethoxycarbonyl, homobenzyloxycarbonyl, tert-butoxycarbonyl, benzyloxycarbonyl and allyloxycarbonyl;

the acyl is selected from the group consisting of formyl, acetyl, trifluoroacetyl and benzoyl;

the sulfonyl is benzenesulfonyl or trifluoromethylsulfonyl.

In the preferred compound of Formula IV, $R^1$ is —$CH_2SR^3$, wherein $R^3$ is methyl; or $R^1$ is —$CH_2OR^4$, wherein $R^4$ is selected from the group consisting of hydrogen, substituted methyl, benzyl, substituted benzyl and silyl, wherein the substituted methyl is methoxymethyl, the substituted benzyl is p-nitrobenzyl, the silyl is tert-butyldimethylsilyl or tert-butyldiphenylsilyl; $R^2$ is selected from the group consisting of formate group, acyl, sulfonyl, benzyl and 4-methoxybenzyl, wherein the formate group is selected from the group consisting of methoxycarbonyl, tert-butoxycarbonyl, benzyloxycarbonyl and allyloxycarbonyl; the acyl is benzoyl; the sulfonyl is benzenesulfonyl or trifluoromethylsulfonyl.

In the further preferred compound of Formula IV, $R^1$ is —$CH_2SR^3$, wherein $R^3$ is methyl; or $R^1$ is —$CH_2OR^4$, wherein $R^4$ is selected from the group consisting of hydrogen, benzyl, and tert-butyldimethylsilyl; $R^2$ is selected from the group consisting of tert-butoxycarbonyl, benzyl, and benzenesulfonyl.

The present invention also provides a process for synthesizing the above-described chiral amino compound of Formula IV with absolute configuration R, which comprises the following steps:

(1) performing a ring opening reaction of a metallic reagent of 2,4,5-trifluorobenzene of Formula III with the aziridine compound of Formula I to form a chiral amino compound of Formula IV with absolute configuration R:

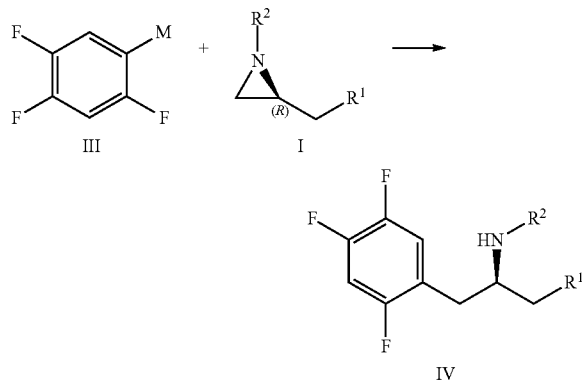

(2) preparing Sitagliptin phosphate of Formula X from the chiral amino-compound of Formula IV:

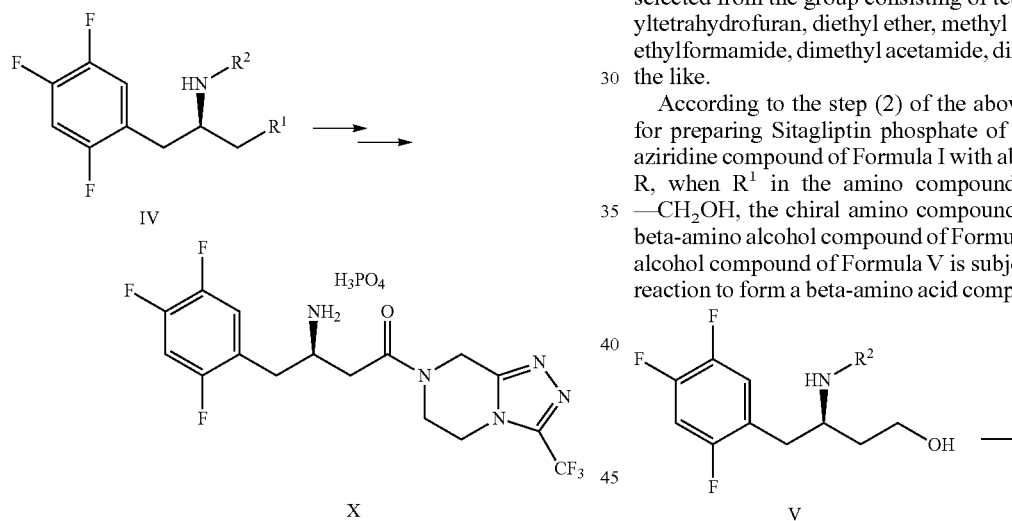

wherein, $R^1$ and $R^2$ in the above reactions are as defined herein, and M is selected from the group consisting of lithium, copper lithium, —Mg.Br, and —Mg.Cl or zinc.

As the above-described metallic reagent of 2,4,5-trifluorobenzene of Formula III, the preferred compound is 2,4,5-trifluorophenyl magnesium bromide. The solvent used in the reaction is an anhydrous solvent selected from the group consisting of tetrahydrofuran, methyltetrahydrofuran, diethyl ether, methyl tert-butyl ether and the like.

According to the step (1) of the above-described process for preparing Sitagliptin phosphate of Formula X from an aziridine compound of Formula I with absolute configuration R, firstly, intramolecularly cyclizing the amino-compound of Formula II with absolute configuration R in the presence of an alkali to form the compound of Formula I:

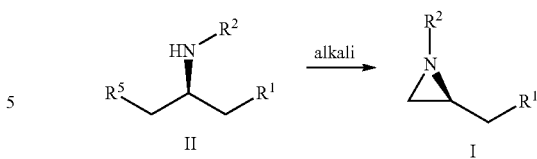

wherein, $R^1$, $R^2$ and $R^5$ in the above reactions are as defined herein.

The alkali used herein includes organic alkali or inorganic alkali; wherein, the inorganic alkali is one or more alkalis selected from the group consisting of sodium hydroxide, potassium hydroxide, lithium hydride, sodium hydride, potassium hydride, calcium hydroxide, sodium carbonate, potassium phosphate and potassium carbonate; the organic alkali is one or more alkalis selected from the group consisting of pyridine, substituted pyridine, piperidine, 1,8-diazabicyclo[5.4.0]undec-7-ene, $C_1$-$C_4$ aliphatic amine, $C_1$-$C_4$ sodium aliphatic alkoxide, $C_1$-$C_4$ potassium aliphatic alkoxide, butyl lithium, lithium diisopropylamide, lithium bis(trimethylsilyl)amide, sodium bis(trimethylsilyl)amide and potassium bis(trimethylsilyl)amide. Preferably, the alkali is sodium hydride or sodium methoxide.

The solvent used in the above steps is an anhydrous solvent selected from the group consisting of tetrahydrofuran, methyltetrahydrofuran, diethyl ether, methyl tert-butyl ether, dimethylformamide, dimethyl acetamide, dimethyl sulfoxide and the like.

According to the step (2) of the above-described process for preparing Sitagliptin phosphate of Formula X from an aziridine compound of Formula I with absolute configuration R, when $R^1$ in the amino compound of Formula IV is —CH$_2$OH, the chiral amino compound of Formula IV is a beta-amino alcohol compound of Formula V. The beta-amino alcohol compound of Formula V is subjected to an oxidation reaction to form a beta-amino acid compound of Formula VI:

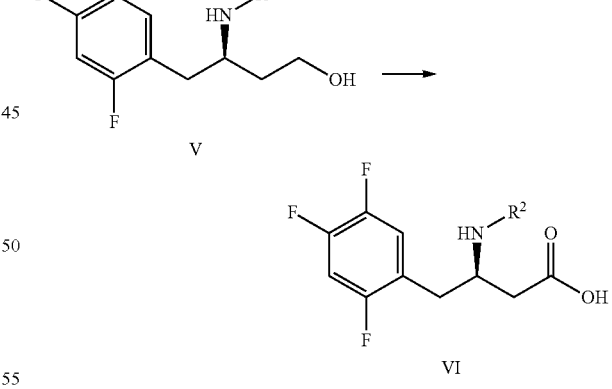

The preparation of beta-amino acid compound of Formula VI from beta-amino alcohol compound of Formula V via oxidation reaction can be achieved by any method publicly-known in the art.

$R^1$ in the amino compound of Formula IV is —CH$_2$SR$^3$, wherein $R^3$ is $C_1$-$C_4$ alkyl; or $R^1$ is —CH$_2$OR$^4$, wherein $R^4$ is selected from the group consisting of methyl, substituted methyl, tetrahydropyranyl, methoxyphenyl, ethyl, benzyl, substituted benzyl and silyl, wherein the substituted methyl is selected from the group consisting of methoxymethyl, methylthiomethyl, benzyloxymethyl, (p-methoxybenzyloxy)methyl, 2-methoxyethoxymethyl and 2-trimethylsilylethoxymethyl; the substituted benzyl is selected from the group consisting of p-methoxybenzyl, 3,4-dimethoxybenzyl and p-nitrobenzyl; the silyl is selected from the group consisting of trimethylsilyl, triethylsilyl, tri-isopropylsilyl, tert-butyldimethylsilyl, tert-butyldiphenylsilyl, diphenylmethylsilyl and tert-butylmethoxyphenylsilyl; firstly, sulphur alkyl or protective group on hydroxyl of the chiral amino compound of Formula IV with configuration R is removed to form a chiral beta-amino alcohol compound of Formula V; then, the beta-amino alcohol compound of Formula V is subjected to an oxidation reaction to form a beta-amino acid compound of Formula VI:

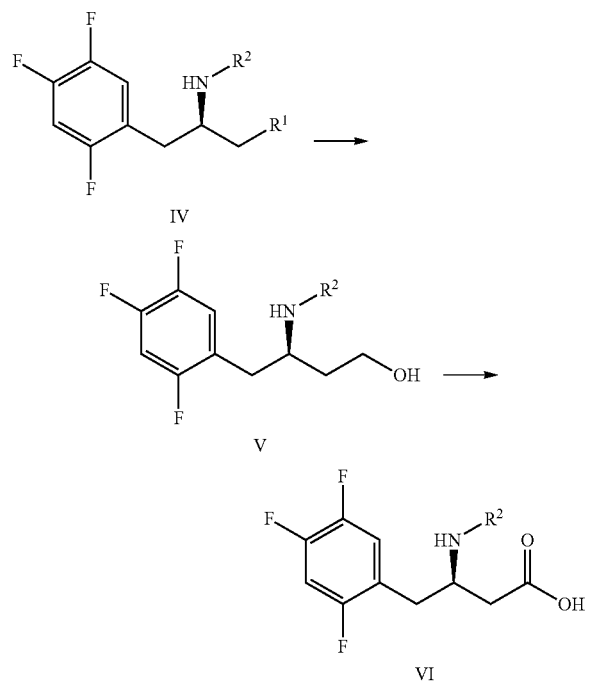

The preparation of chiral beta-amino alcohol compound of Formula V with configuration R via removing sulphur alkyl or hydroxyl protective group from chiral amino-compound of Formula IV with configuration R can be achieved by any method publicly-known in the art.

For example, in the above reactions, when $R^1$ is —$CH_2SCH_3$, i.e., the compound of Formula IV is characterized by the following structural formula IV-1, the present invention provides a process for synthesizing the compound of Formula V via removing methylthio group of the compound of Formula IV-1, which comprises reacting the compound of Formula IV-1 with iodomethane at room temperature or low temperature in an alcohol solvent (such as methanol and ethanol) to form a sulfonium salt, followed by hydrolization to form the compound of Formula V:

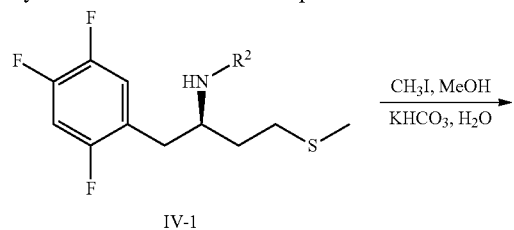

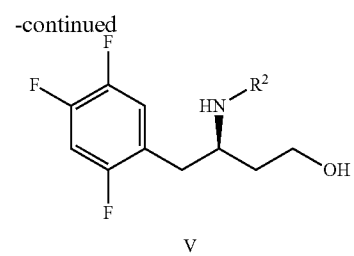

In the above reactions, when $R^1$ is —$CH_2OR^4$ (wherein $R^4$ is hydrogen, benzyl, tert-butyldimethylsilyl), i.e., the compound of Formula IV is characterized by the following structural Formula IV-2, the present invention provides a process for synthesizing the compound of Formula V via removing protective group on hydroxyl from the compound of Formula IV-2, i.e., removing corresponding protective group on hydroxyl of the compound of Formula IV-2 via suitable methods. For example, when $R^4$ is benzyl in the present invention, the removal of benzyl can be accomplished by catalytic hydrogenation with Pd/C catalyst in an alcohol solvent such as methanol. For another example, when $R^4$ is tert-butyldimethylsilyl in the present invention, the removal of tert-butyldimethylsilyl can be accomplished by reacting with a special reagent for removing silyl protective group, such as tetrabutyl ammonium fluoride, at room temperature or heating condition and in the presence of an alcohol solvent such as methanol.

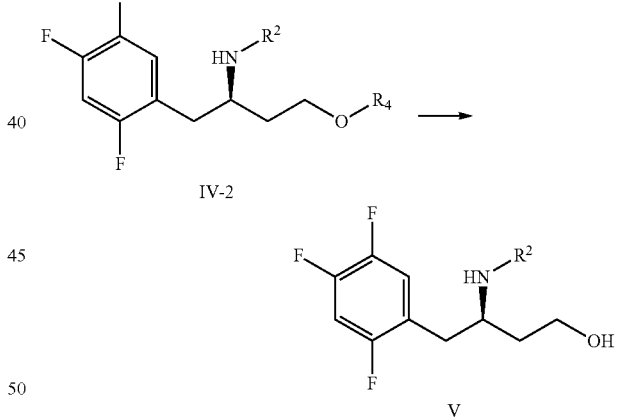

In the above-described process of preparing Sitagliptin phosphate of Formula X from an aziridine compound of Formula I with absolute configuration R, the beta-amino alcohol compound of Formula V is subjected to an oxidation reaction to form a beta-amino acid compound of Formula VI:

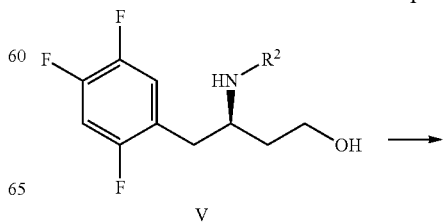

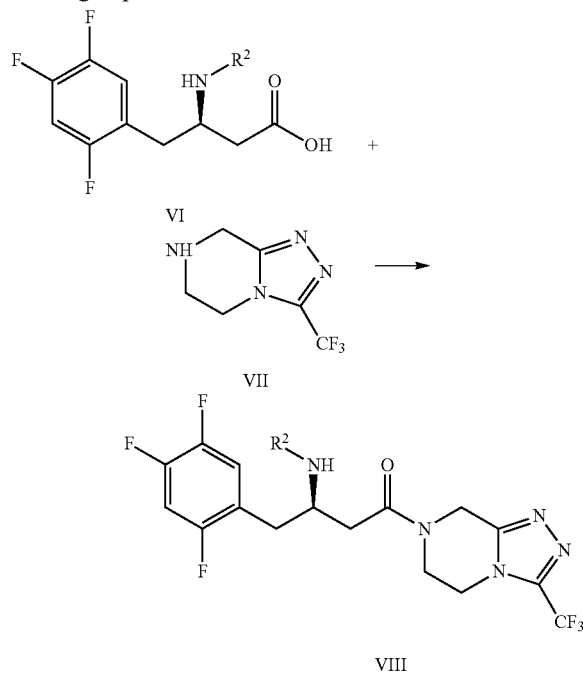

VI wherein, $R^2$ in the above reactions is as defined herein.

The present invention provides a process of oxidizing the compound of Formula V to the beta-amino acid compound of Formula VI. For example, it is achieved by oxidizing a primary alcohol to acid with sodium hypochlorite under the catalyzing of TEMPO to prepare the beta-amino acid compound of Formula VI.

In the above-described process of preparing Sitagliptin phosphate of Formula X from an aziridine compound of Formula I with absolute configuration R, the beta-amino acid compound of Formula VI is subjected to a condensation reaction with a triazosin compound of Formula VII to form a Sitagliptin derivative of Formula VIII having a protected amino-group:

VI
+
VII

→

VIII wherein, $R^2$ in the above reaction is as defined herein.

The present invention further provides a method for forming peptide bond between a beta-amino acid compound of Formula VI and the triazosin compound of Formula VII. For example, it is achieved by reacting the beta-amino acid compound of Formula VI with the triazosin compound of Formula VII at room temperature in a solvent such as acetonitrile or dichloromethane, as well as in the presence of a condensation reagent such as DCC or EDCI and an organic alkali such as triethylamine, to obtain the Sitagliptin derivative of Formula VIII having a protected amino-group with high yield.

In the above-described process of preparing Sitagliptin phosphate of Formula X from an aziridine compound of Formula I with absolute configuration R, the protective group $R^2$ on amino-group is removed from the Sitagliptin derivative of Formula VIII having a protected amino-group to form Sitagliptin of Formula IX:

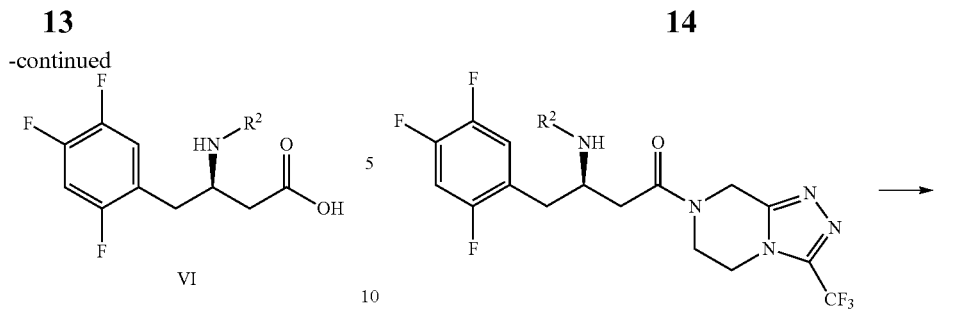

VIII

→

IX wherein, $R^2$ in the above reaction is as defined herein.

The present invention provides a synthesis method of Sitagliptin of Formula IX via removing the protective group on amino group from the compound of Formula VIII, i.e., when $R^2$ is tert-butoxycarbonyl, benzyl or benzenesulfonyl, the corresponding protective group on amino group of the compound of Formula VIII will be removed via suitable methods, respectively. For example, when $R^2$ is tert-butoxycarbonyl, the removal of tert-butoxycarbonyl can be achieved by reacting with a strong acid like hydrochloric acid at room temperature or heating condition and in the presence of an alcohol solvent. For another example, when $R^2$ is benzyl, the removal of benzyl can be accomplished by catalytic hydrogenation with Pd/C catalyst in the presence of an alcohol solvent such as methanol.

In the above-described process of preparing Sitagliptin phosphate of Formula X from an aziridine compound of Formula I with absolute configuration R, Sitagliptin of Formula IX reacts with phosphoric acid to form Sitagliptin phosphate of Formula X:

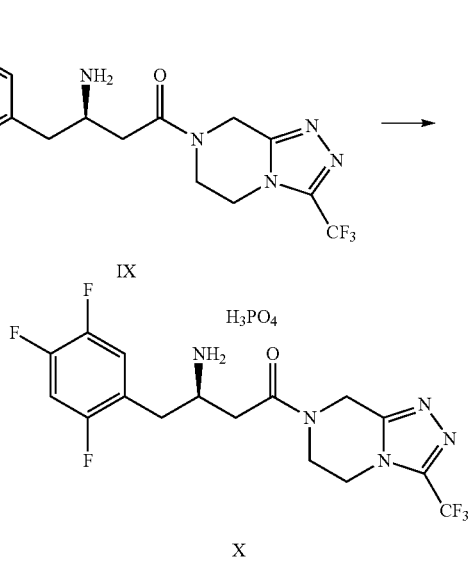

IX $H_3PO_4$

X

There are several beneficial technical effects brought by the present invention.

The present invention is advantageous in that a cheap and readily available chiral amino compound is used as the starting material which is subjected to cyclizing to form a chiral aridine compound of Formula I, which is further undergone a nucleophilic addition reaction with a metallic reagent of trifluorobenzene to form a precursor compound for preparing Sitagliptin, i.e., the chiral amino-alcohol compound of Formula V. The precursor compound was then converted into Sitagliptin via oxidization, condensation and removal of protective group respectively.

It has been shown experimentally during the development of synthesis of chiral aziridine compound of Formula I that when $R^1$ is an ester group (i.e. —$CO_2R$) or hydroxyl methyl sulphonic acid ester (—$CH_2OMs$ or —$CH_2OTs$) or halogenated hydroxymethyl (—$CH_2X$), the aziridine compound is subjected to a nucleophilic addition reaction with the metallic reagent of trifluorobenzene, the metallic reagent of trifluorobenzene not only performs ring-opening reaction with the aziridine compound, but also reacts simultaneously with the ester group (i.e. —$CO_2R$) or hydroxylmethyl sulphonic acid ester (—$CH_2OMs$ or —$CH_2OTs$) or halogenated hydroxymethyl (—$CH_2X$), which results in a poor reaction selectivity and complicated reaction system. Accordingly, the present invention provides the above-described chiral aziridine compound of Formula I which only possess a single reactive site when it is subjected to a nucleophilic addition reaction with the metallic reagent of trifluorobenzene and thus the reaction selectivity is higher.

Furthermore, compared with the reported or industrialized synthesizing process, the process of using the chiral aziridine compound of Formula I to synthesize Sitagliptin phosphate according to the present invention is advantageous in that a chiral center can be introduced by the chiral material, without having to build chirality of amino-group with various complicated chiral reagents and avoiding a chiral asymmetric catalytic hydrogenation. The process is simple without using expensive elements, eco-friendly and low cost of raw materials.

DETAILED DESCRIPTION OF THE INVENTION

The present invention will be further illustrated by the following examples which are not intended to limit the scope of the present invention in any way.

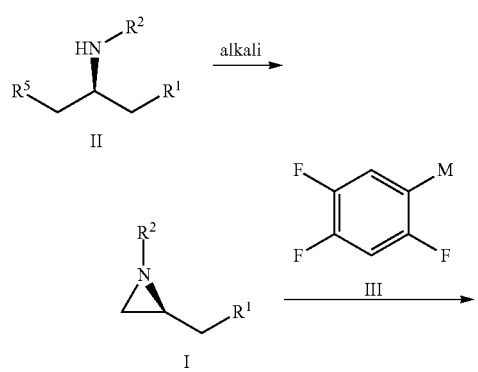

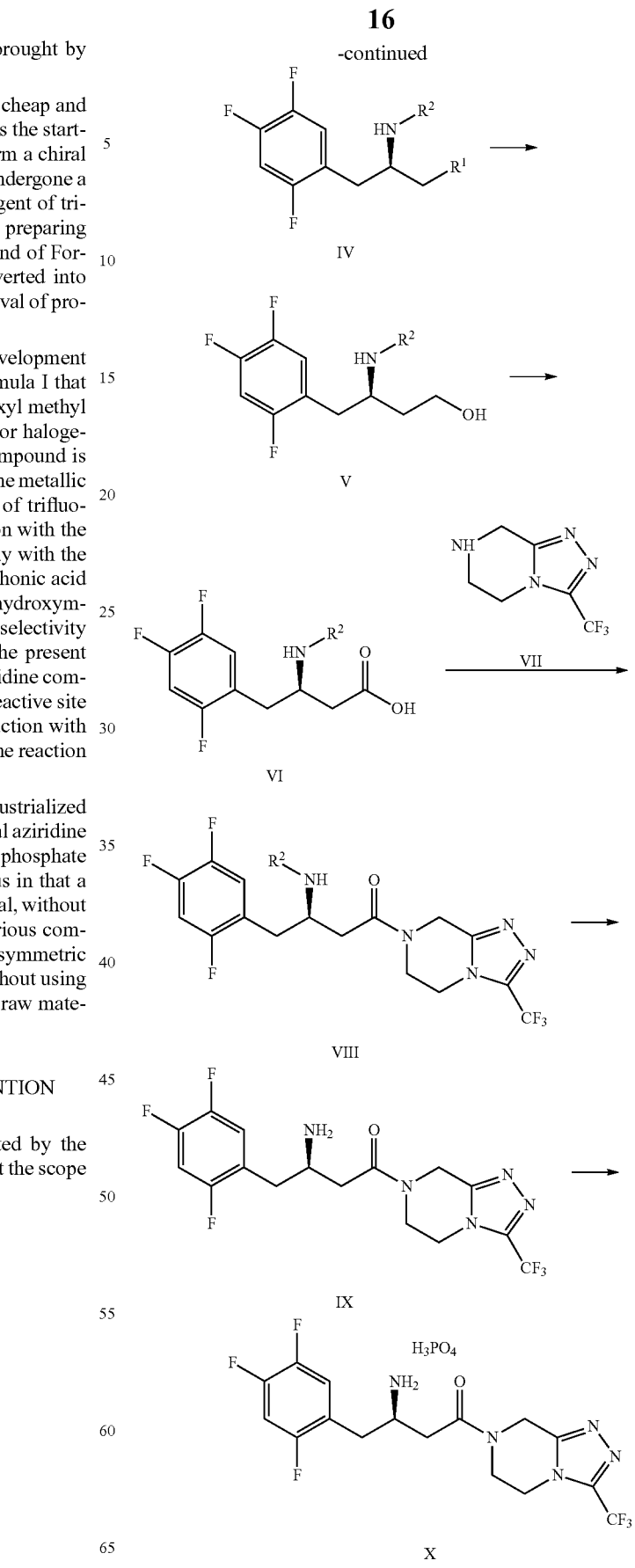

Example 1

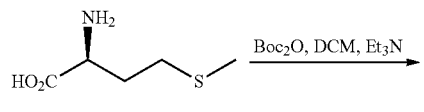

7.2 g Methionine was dissolved in a mixture of 50 mL water and 50 mL acetonitrile. To this solution was added 2 g NaOH (0.05 mol). The obtained mixture was cooled down to 0° C. and then 10.9 g di-t-butyl dicarbonate (0.05 mol) was added. After addition, the mixture was warmed to room temperature (24-25° C.) and reacted for 12 h. Acetonitrile was removed by distillation. Potassium carbonate was added to the residue and the pH thereof was adjusted to 12. After extracted with 50 mL dichloromethane twice, the organic layers were discarded. To the aqueous layer was added 1N dilute hydrochloric acid to adjust the pH to 6. After extracted with 50 mL dichloromethane twice, the organic layers were collected together and washed with 50 mL saturate solution of sodium chloride and then dried over anhydrous sodium sulfate, followed by concentration to obtain a viscous product (11.4 g). The yield was 95%.

$^1$H NMR (500 MHz, CDCl$_3$) δ 11.62 (br, 1H), 6.91 (br, 1H), 4.40 (m. 1H), 2.52 (t, J=4.8 Hz, 2H), 2.05 (s, 3H), 1.92~2.15 (m. 2H), 1.42 (s, 9H). Ms (M$^+$+1): 250.

Example 2

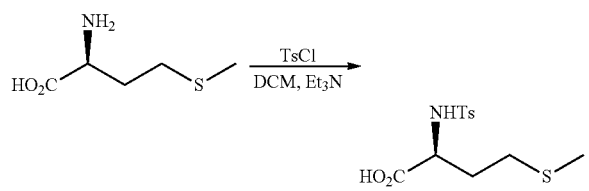

7.5 g Methionine (0.05 mol) was dissolved in 100 mL dichloromethane. To this solution was added triethylamine (10.5 ml, 0.075 mol). The reaction mixture was cooled down to 0° C. and then p-toluensulfonyl chloride (11.5 g, 0.06 mol) was added dropwise. After addition, the mixture was warmed to room temperature and reacted for 12 h. 20 mL Water was added to quench the reaction and then potassium carbonate was added to adjust the pH to 12. After extracted with 50 mL dichloromethane twice, the organic layers were discarded. To the aqueous layer was added 1N dilute hydrochloric acid to adjust the pH to 6. After extracted with 50 mL dichloromethane twice, the organic layers were collected together and washed with 50 mL saturate solution of sodium chloride and then dried over anhydrous sodium sulfate, followed by concentration to obtain a viscous product (13.2 g). The yield was 91%.

$^1$H NMR (400 MHz, CDCl$_3$) δ 8.06~7.76 (m, 2H), 7.59 (t, J=6.6 Hz, 3H), 6.35 (s, 1H), 3.86 (t, J=6.6 Hz, 1H), 2.70 (s, 2H), 2.35 (s, 3H), 2.21 (s, 1H), 2.15 (s, 3H), 2.12 (s, 1H). Ms (M$^+$+1): 304.

Example 3

7.5 g Methionine (0.05 mol) was dissolved in 100 mL dichloromethane. To this solution was added triethylamine (10.5 ml, 0.075 mol). The reaction mixture was cooled down to 0° C. and then benzoyl chloride (8.4 g, 0.06 mol) was added dropwise. After addition, the mixture was warmed to room temperature and reacted for 12 h. 20 mL Water was added to quench the reaction and then potassium carbonate was added to adjust the pH to 12. After extracted with 50 mL dichloromethane twice, the organic layers were discarded. To the aqueous layer was added 1N dilute hydrochloric acid to adjust the pH to 6. After extracted with 50 mL dichloromethane twice, the organic layers were collected together and washed with 50 mL saturate solution of sodium chloride and then dried over anhydrous sodium sulfate, followed by concentration to obtain a viscous product (9.9 g). The yield was 78%.

$^1$H NMR (400 MHz, CDCl$_3$) δ 8.41 (s, 1H), 7.98~7.67 (m, 2H), 7.58 (s, 1H), 7.54~7.33 (m, 2H), 4.53 (s, 1H), 2.72 (s, 2H), 2.36 (s, 3H), 2.22 (d, J=27.6 Hz, 2H). Ms (M$^+$+1): 254.

Example 4

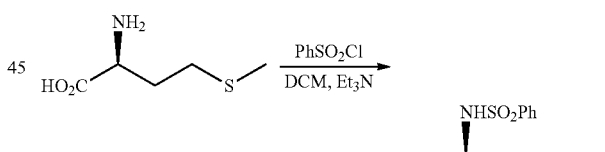

7.5 g Methionine (0.05 mol) was dissolved in 100 mL dichloromethane. To this solution was added triethylamine (10.5 ml, 0.075 mol). The reaction mixture was cooled down to 0° C. and then benzoyl chloride (10.6 g, 0.06 mol) was added dropwise. After addition, the mixture was warmed to room temperature and reacted for 12 h. 20 mL Water was added to quench the reaction and then potassium carbonate was added to adjust the pH to 12. After extracted with 50 mL dichloromethane twice, the organic layers were discarded. To the aqueous layer was added 1N dilute hydrochloric acid to adjust the pH to 6. After extracted with 50 mL dichloromethane twice, the organic layers were collected together and washed with 50 mL saturate solution of sodium chloride and then dried over anhydrous sodium sulfate, followed by concentration to obtain a viscous product (12.9 g). The yield was 89%.

$^1$H NMR (400 MHz, CDCl$_3$) δ 8.06~7.76 (m, 2H), 7.59 (t, J=6.6 Hz, 3H), 6.35 (s, 1H), 3.86 (t, J=6.6 Hz, 1H), 2.70 (s, 2H), 2.21 (s, 1H), 2.15 (s, 3H), 2.12 (s, 1H). Ms (M$^+$+1): 290.

Example 5

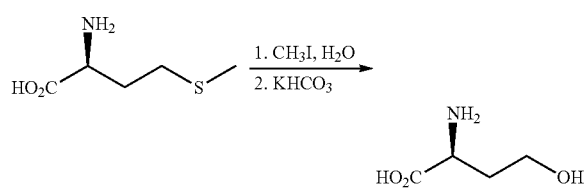

Into a 500 mL three-necked flask, 15 g L-methionine (0.1 mol) and 300 mL water were added at room temperature, then 38.4 g iodomethane (0.3 mol) was added dropwise and the mixture reacted for 24 h under a nitrogen balloon. The reaction mixture was concentrated to 200 mL and the excess iodomethane was removed under reduced pressure. The concentrated mixture was heated to reflux. 10 g KHCO$_3$ (0.1 mol) was dissolved in 50 mL water and the obtained solution was dropwisely added slowly to the above mixture through a dropping funnel. The pH value of the mixture was maintained between 3-6 by controlling the speed of addition. After finishing the addition, the reaction was refluxed for another 10 h. The solvent was removed under reduced pressure. 200 mL Solution with the ratio of methanol:water=100:1 was added. Then concentrated hydrochloric acid was added dropwise to adjust the pH to 5-6. The salt was filtered off while it is hot and the solution was concentrated to 50 mL. After freezing crystallization, suction filtration and drying, 8.8 g L-methionine was obtained as a white solid. The yield was 74%.

Example 6

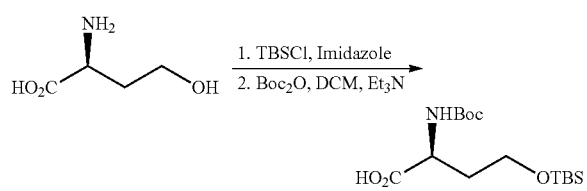

Into a 100 mL three-necked flask were added 5 g homoserine (0.042 mol) and 50 mL DMF. The mixture was cooled down to 0° C. and 3.4 g imidazole (0.05 mol) was added. TBSCl (6.6 g, 0.044 mol) was then added in portions under nitrogen. After addition, the mixture was warmed to room temperature and stirred for 16 h, 10 mL water was added to quench the reaction. The solvent was concentrate under reduced pressure, and 50 mL water and 50 mL dichloromethane were then added. After separation, the aqueous layer was extracted with another 50 mL dichloromethane again. The organic layers were collected together and washed with another 50 mL saturated solution of sodium chloride, and then dried over anhydrous sodium sulfate, followed by concentration to obtain a viscous product.

The crude product obtained from the above reaction was dissolved in a mixture of 50 mL water and 50 mL acetonitrile. To this solution was added NaOH (2 g, 0.05 mol). The obtained mixture was cooled down to 0° C. and then 10.9 g di-t-butyl dicarbonate (0.05 mol) was added. After addition, the mixture was warmed to room temperature and reacted for 12 h. Acetonitrile was removed by distillation. To the residue was added potassium carbonate to adjust the pH to 12. After extracted with 50 mL dichloromethane twice, the organic layers were discarded. To the aqueous layer was added 1N dilute hydrochloric acid to adjust the pH to 6. After extracted with 50 mL dichloromethane twice, the organic layers were collected together and washed with 50 mL saturate solution of sodium chloride and then dried over anhydrous sodium sulfate, followed by concentration to obtain a viscous product (11.3 g). The yield was 81%.

$^1$H NMR (500 MHz, CDCl$_3$) δ 8.04 (br, 1H), 5.86 (d, J=6.7 Hz, 1H), 4.61~4.13 (m, 1H), 3.94~3.62 (m, 2H), 2.19~2.04 (m, 1H), 2.04~1.91 (m, 1H), 1.44 (s, 9H), 0.90 (s, 9H), 0.08 (d, J=12.9 Hz, 6H). Ms (M$^+$+1): 334.

Example 7

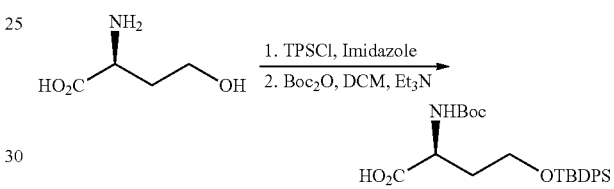

Into a 100 mL three-necked flask were added 5 g homoserine (0.042 mol) and 50 mL DMF. The mixture was cooled down to 0° C. and 3.4 g imidazole (0.05 mol) was added. TBDPSCl (12.1 g, 0.044 mol) was then added in portions under nitrogen. After addition, the mixture was warmed to room temperature and stirred for 16 h, 10 mL water was added to quench the reaction. The solvent was concentrate under reduced pressure, then 50 mL water and 50 mL dichloromethane were added. After separation, the aqueous layer was extracted with another 50 mL dichloromethane. The organic layers were collected together and washed with another 50 mL saturated solution of sodium chloride, and then dried over anhydrous sodium sulfate, followed by concentration to obtain a viscous product.

The crude product obtained from the above reaction was dissolved in a mixture of 50 mL water and 50 mL acetonitrile. To this solution was added NaOH (2 g, 0.05 mol). The obtained mixture was cooled down to 0° C. and then 10.9 g di-t-butyl dicarbonate (0.05 mol) was added. After addition, the mixture was warmed to room temperature and reacted for 12 h. Acetonitrile was removed by distillation. To the residue was added potassium carbonate to adjust the pH to 12. After extracted with 50 mL dichloromethane twice, the organic layers were discarded. To the aqueous layer was added 1N dilute hydrochloric acid to adjust the pH to 6. After extracted with 50 mL dichloromethane twice, the organic layers were collected together and washed with 50 mL saturate solution of sodium chloride and then dried over anhydrous sodium sulfate, followed by concentration to obtain a viscous product (14.4 g). The yield was 75%.

$^1$H NMR (500 MHz, CDCl$_3$) δ 8.04 (br, 1H), 7.35~7.62 (m, 10H), 5.86 (d, J=6.7 Hz, 1H), 4.61~4.13 (m, 1H), 3.94~3.62 (m, 2H), 2.19~2.04 (m, 1H), 2.04~1.91 (m, 1H), 1.44 (s, 9H), 0.90 (s, 9H). Ms (M$^+$+1): 459.

Example 8

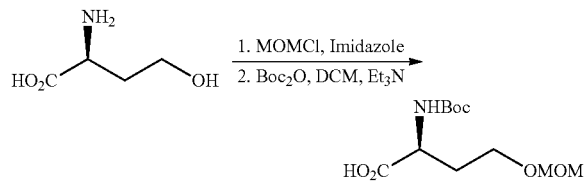

Into a 100 mL three-necked flask were added 5 g homoserine (0.042 mol) and 50 mL DCM. The mixture was cooled down to 0° C. and 3.4 g imidazole (0.05 mol) was added. MOMCl (3.52 g, 0.044 mol) was then added in portions under nitrogen. After addition, the mixture was warmed to room temperature and stirred for 8 h. 10 mL Water was added to quench the reaction. The solvent was concentrate under reduced pressure, then 50 mL water and 50 mL dichloromethane were added. After separation, the aqueous layer was extracted with another 50 mL dichloromethane. The organic layers were collected together and washed with another 50 mL saturated solution of sodium chloride, and then dried over anhydrous sodium sulfate, followed by concentration to obtain a viscous product.

The crude product obtained from the above reaction was dissolved in a mixture of 50 mL water and 50 mL acetonitrile. To this solution was added NaOH (2 g, 0.05 mol). The obtained mixture was cooled down to 0° C. and then 10.9 g di-t-butyl dicarbonate (0.05 mol) was added. After addition, the mixture was warmed to room temperature and reacted for 12 h. Acetonitrile was removed by distillation. To the residue was added potassium carbonate to adjust the pH to 12. After extracted with 50 mL dichloromethane twice, the organic layers were discarded. To the aqueous layer was added 1N dilute hydrochloric acid to adjust the pH to 6. After extracted with 50 mL dichloromethane twice, the organic layers were collected together and washed with 50 mL saturate solution of sodium chloride and then dried over anhydrous sodium sulfate, followed by concentration to obtain a viscous product (7.8 g). The yield was 71%.

$^1$H NMR (500 MHz, CDCl$_3$) δ 8.04 (br, 1H), 5.86 (d, J=6.7 Hz, 1H), 4.61~4.13 (m, 1H), 4.60 (s, 3H), 3.94~3.62 (m, 2H), 3.52 (s, 3H), 2.19~2.04 (m, 1H), 2.04~1.91 (m, 1H), 1.44 (s, 9H). Ms (M$^+$+1): 264.

Example 9

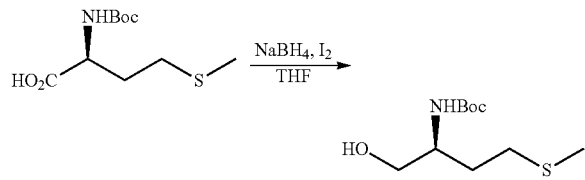

Into a 500 mL three-necked flask were added the starting compound as shown in the above route (49.8 g, 0.5 mol) and 250 mL tetrahydrofuran. The temperature of the reaction mixture was adjusted to about 0-5° C. in an ice-salt bath with agitation. To this mixture, sodium borohydride (19 g, 0.5 mol) was added slowly, followed by the addition of 50 mL methanol. After addition, 100 mL solution of iodine (127 g, 0.5 mol) in tetrahydrofuran was added. Then, the reaction system was warmed to reflux. The reaction was continued for 2 h under agitation. After the raw material was consumed under the detecting of TLC, the temperature of the reaction mixture was adjusted with an ice-water bath. Saturated solution of ammonia chloride was added to quench the reaction. After 100 mL THF was evaporated out by a rotary evaporator under reduced pressure, the residue was extracted with ethyl acetate (300 mL×2). The obtained organic layer was washed with dilute hydrochloric acid, followed by saturated sodium hydrogen carbonate, and finally aqueous solution of sodium chloride. After drying and concentrating, a crude product (120 g) was obtained as an oil. The crude product was further treated by column chromatography to obtain a purified product (97.5 g). The yield was 85%.

$^1$H NMR (400 MHz, CDCl$_3$) δ 11.64 (br, 1H), 6.85 (br, 1H), 4.55~4.48 (m, 1H), 2.53 (t, J=4.9 Hz, 2H), 3.44 (s, 3H), 2.05 (s, 3H), 2.02~1.87 (m, 2H), 1.48 (s, 9H). Ms (M$^+$+1): 236.

Example 10

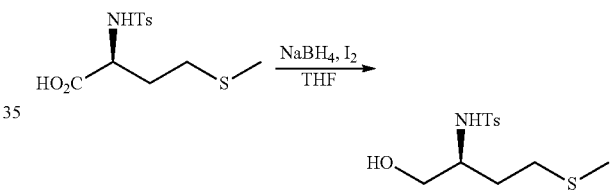

Into a 2 L three-necked flask were added the starting compound as shown in the above route (151.5 g, 0.5 mol) and 1000 mL tetrahydrofuran. The temperature of the reaction mixture was adjusted to about 0-5° C. with an ice-salt bath under agitation. To this mixture, sodium borohydride (19 g, 0.5 mol) was added slowly, followed by the addition of 150 mL methanol and then 500 mL solution of iodine (127 g, 0.5 mol) in tetrahydrofuran was added dropwise. After addition, the reaction system was warmed to reflux. The reaction was continued for 2 h under agitation. After the raw material was consumed under the detecting of TLC, the temperature of the reaction mixture was adjusted with an ice-water bath. Saturated solution of ammonia chloride was added to quench the reaction. After 1200 mL THF was evaporated out by a rotary evaporator under reduced pressure, the residue was extracted with ethyl acetate (500 mL×2). The obtained organic layer was washed with dilute hydrochloric acid, followed by saturated sodium hydrogen carbonate, and finally aqueous solution of sodium chloride. After drying and concentrating, a crude product (120 g) was obtained as an oil. The crude product was further treated by column chromatography to obtain a purified product (108 g). The yield was 75%.

$^1$H NMR (400 MHz, CDCl$_3$) δ 7.91~7.76 (m, 2H), 7.58 (t, J=8.1 Hz, 3H), 5.47 (s, 1H), 3.90 (s, 1H), 3.55 (s, 1H), 3.20 (s, 1H), 2.58 (s, 2H), 2.36 (s, 3H), 2.32 (s, 3H), 1.85 (s, 2H), 1.44 (s, 1H). Ms (M$^+$+1): 290.

Example 11

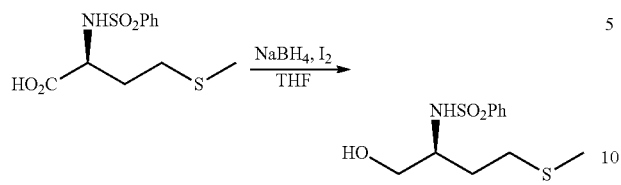

Into a 500 mL three-necked flask were added the starting compound as shown in the above route (144.5 g, 0.5 mol) and 250 mL tetrahydrofuran. The temperature of the reaction mixture was adjusted to about 0-5° C. with an ice-salt bath under agitation. To this mixture, sodium borohydride (19 g, 0.5 mol) was added slowly, followed by the addition of 50 mL methanol and then 100 mL solution of iodine (127 g, 0.5 mol) in tetrahydrofuran was added dropwise. After addition, the reaction system was warmed to reflux. The reaction was continued for 2 h under agitation. After the raw material was consumed under the detecting of TLC, the temperature of the reaction mixture was adjusted with an ice-water bath. Saturated solution of ammonia chloride was added to quench the reaction. After 100 mL THF was evaporated out by a rotary evaporator under reduced pressure, the residue was extracted with ethyl acetate (300 mL×2). The obtained organic layer was washed with dilute hydrochloric acid, followed by saturated sodium hydrogen carbonate, and finally aqueous solution of sodium chloride. After drying and concentrating, a crude product (130.5 g) was obtained as an oil. The crude product was further treated by column chromatography to obtain a purified product (114.1 g). The yield was 83%.

$^1$H NMR (400 MHz, CDCl$_3$) δ 7.91~7.76 (m, 2H), 7.58 (t, J=8.1 Hz, 3H), 5.47 (s, 1H), 3.90 (s, 1H), 3.55 (s, 1H), 3.20 (s, 1H), 2.58 (s, 2H), 2.32 (s, 3H), 1.85 (s, 2H), 1.44 (s, 1H). Ms (M$^+$+1): 276.

Example 12

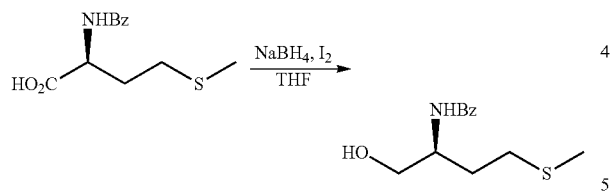

Into a 500 mL three-necked flask were added the starting compound as shown in the above route (126.5 g, 0.5 mol) and 250 mL tetrahydrofuran. The temperature of the reaction mixture was adjusted to about 0-5° C. with an ice-salt bath under agitation. To this mixture, sodium borohydride (19 g, 0.5 mol) was added slowly, followed by the addition of 50 mL methanol and then 100 mL solution of iodine (127 g, 0.5 mol) in tetrahydrofuran was added dropwise. After addition, the reaction system was warmed to reflux. The reaction was continued for 2 h under agitation. After the raw material was consumed under the detecting of TLC, the temperature of the reaction mixture was adjusted with an ice-water bath. Saturated solution of ammonia chloride was added to quench the reaction. After 100 mL THF was evaporated out by a rotary evaporator under reduced pressure, the residue was extracted with ethyl acetate (300 mL×2). The obtained organic layer was washed with dilute hydrochloric acid, followed by saturated sodium hydrogen carbonate, and finally aqueous solution of sodium chloride. After drying and concentrating, a crude product (85 g) was obtained as an oil. The crude product was further treated by column chromatography to obtain a purified product (72.9 g). The yield was 61%.

$^1$H NMR (400 MHz, CDCl$_3$) δ 7.84~7.69 (m, 2H), 7.64~7.38 (m, 3H), 6.69 (s, 1H), 4.01 (br, 1H), 3.87-3.75 (m, 1H), 3.63 (s, 1H), 2.52 (s, 2H), 2.38 (s, 3H), 2.08 (s, 1H), 1.89-1.82 (m, 1H), 1.44~1.38 (m, 1H). Ms (M$^+$+1): 240.

Example 13

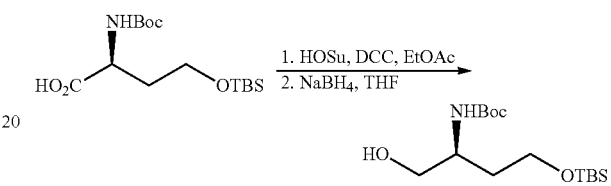

Into a 100 mL three-necked flask were added the starting compound as shown in the above route (8.5 g, 0.025 mol) and 50 mL ethyl acetate. The obtained mixture was cooled down to 0° C. and 3.14 g HOSu (0.027 mol) was added. The solution of DCC (5.27 g, 0.026 mol) dissolved in 20 mL ethyl acetate was slowly added dropwise to the above reaction mixture. After addition, the mixture was warmed to room temperature and reacted for 8 h. A large amount of insoluble substance produced in the reaction was filtered off. The obtained filtrate was washed with 100 mL saturated sodium hydrogen carbonate and aqueous solution of sodium chloride successively, then dried over anhydrous sodium sulfate, followed by filtration and concentration to obtain a milk white oil. At 0° C., sodium borohydride (0.95 g, 0.025 mol) was dissolved in a mixture of water (5 ml) and tetrahydrofuran (40 mL). After the milk white oil was dissolved in 10 mL ethyl acetate, the obtained mixture was immediately poured into the above sodium borohydride solution. After 5 min, 50 mL saturated solution of ammonia chloride was added to quench the reaction. The aqueous layer was extracted with 50 mL ethyl acetate and the organic layer was washed with saturated solution of sodium chloride and then dried over anhydrous sodium sulfate, followed by filtration and concentration to obtain a crude product which was further treated by column chromatography to obtain a viscous product (5.2 g). The yield was 65%.

$^1$H NMR (400 MHz, CDCl$_3$) δ 5.74~5.26 (m, 1H), 3.74 (t, J=5.3 Hz, 3H), 3.72~3.58 (m, 2H), 3.51 (s, 1H), 1.83 (s, 1H), 1.73 (d, J=6.1 Hz, 1H), 1.45 (s, 9H), 0.90 (s, 9H), 0.07 (d, J=12.4 Hz, 6H). Ms (M$^+$+1): 320.

Example 14

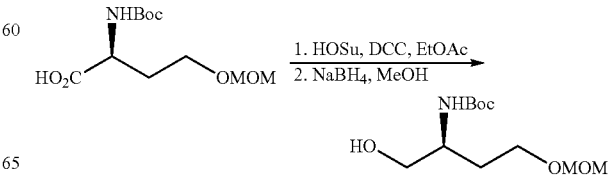

Into a 100 mL three-necked flask were added the starting compound as shown in the above route (13.2 g, 0.025 mol) and 50 mL ethyl acetate. The obtained mixture was cooled down to 0° C. and 3.14 g HOSu (0.027 mol) was added. The solution of DCC (5.27 g, 0.026 mol) dissolved in 20 mL ethyl acetate was slowly added dropwise to the above reaction mixture. After addition, the mixture was warmed to room temperature and reacted for 8 h. A large amount of insoluble substance produced in the reaction was filtered off. The obtained filtrate was washed with 100 mL saturated sodium hydrogen carbonate and aqueous solution of sodium chloride successively, then dried over anhydrous sodium sulfate, followed by filtration and concentration to obtain a milk white oil. At 0° C., sodium borohydride (0.95 g, 0.025 mol) was dissolved in a mixture of water (5 ml) and tetrahydrofuran (40 mL). After the milk white oil was dissolved in 10 mL ethyl acetate, the obtained mixture was immediately poured into the above sodium borohydride solution. After 5 min, 50 mL saturated solution of ammonia chloride was added to quench the reaction. The aqueous layer was extracted with 50 mL ethyl acetate and the organic layer was washed with saturated solution of sodium chloride and then dried over anhydrous sodium sulfate, followed by filtration and concentration to afford a crude product which was further treated by column chromatography to obtain a viscous product (3.9 g). The yield was 62%.

$^1$H NMR (400 MHz, CDCl$_3$) δ 6.09 (s, 1H), 4.50 (s, 2H), 4.21~4.18 (m, 1H), 3.78 (s, 1H), 3.59 (s, 1H), 3.40 (s, 3H), 3.33~3.19 (m, 2H), 1.90 (s, 1H), 1.71 (s, 1H), 1.49 (s, 9H), 1.44 (s, 1H). Ms (M$^+$+1): 320. Ms (M$^+$+1): 250.

Example 15

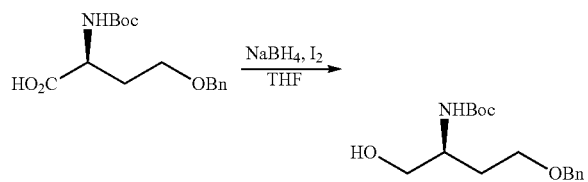

Into a 500 mL three-necked flask were added the starting compound as shown in the above route (154.5 g, 0.5 mol) and 250 mL tetrahydrofuran. The temperature of the reaction mixture was adjusted to about 0-5° C. with an ice-salt bath under agitation. To this mixture, sodium borohydride (19 g, 0.5 mol) was added slowly, followed by the addition of 50 mL methanol and then 100 mL solution of iodine (127 g, 0.5 mol) in tetrahydrofuran was added dropwise. After addition, the reaction system was warmed to reflux. The reaction was continued for 2 h under agitation. After the raw material was consumed under the detecting of TLC, the temperature of the reaction mixture was adjusted with an ice-water bath. Saturated solution of ammonia chloride was added to quench the reaction. After 100 mL THF was evaporated out by a rotary evaporator under reduced pressure, the residue was extracted with ethyl acetate (300 mL×2). The obtained organic layer was washed with dilute hydrochloric acid, followed by saturated sodium hydrogen carbonate, and finally aqueous solution of sodium chloride. After drying and concentrating, a crude product (150 g) was obtained as an oil. The crude product was further treated by column chromatography to obtain a purified product (126.8 g). The yield was 86%.

$^1$H NMR (400 MHz, CDCl$_3$) δ 7.53~7.22 (m, 5H), 5.74~5.26 (m, 1H), 3.74 (t, J=5.3 Hz, 3H), 3.72~3.58 (m, 2H), 3.51 (s, 2H), 3.11 (br, 1H), 1.83 (s, 1H), 1.73 (d, J=6.1 Hz, 1H), 1.45 (s, 9H). Ms (M$^+$+1): 296.

Example 16

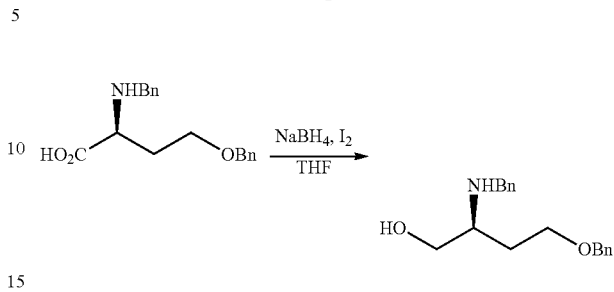

Into a 500 mL three-necked flask were added the starting compound as shown in the above route (149.5 g, 0.5 mol) and 250 mL tetrahydrofuran. The temperature of the reaction mixture was adjusted to about 0-5° C. with an ice-salt bath under agitation. To this mixture, sodium borohydride (19 g, 0.5 mol) was added slowly, followed by the addition of 50 mL methanol and then 100 mL solution of iodine (127 g, 0.5 mol) in tetrahydrofuran was added dropwise. After addition, the reaction system was warmed to reflux. The reaction was continued for 2 h under agitation. After the raw material was consumed under the detecting of TLC, the temperature of the reaction mixture was adjusted with an ice-water bath. Saturated solution of ammonia chloride was added to quench the reaction. After 100 mL THF was evaporated out by a rotary evaporator under reduced pressure, the residue was extracted with ethyl acetate (300 mL×2). The obtained organic layer was washed with dilute hydrochloric acid, followed by saturated sodium hydrogen carbonate, and finally aqueous solution of sodium chloride. After drying and concentrating, a crude product (145 g) was obtained as an oil. The crude product was further treated by column chromatography to obtain a purified product (129.7 g). The yield was 91%.

$^1$H NMR (400 MHz, CDCl$_3$) δ 7.33~7.18 (m, 10H), 4.77 (s, 2H), 4.05 (d, J=6.3 Hz, 2H), 3.75 (s, 1H), 3.62 (s, 1H), 3.53 (s, 2H), 3.43 (s, 1H), 3.27 (s, 1H), 1.66 (s, 1H), 1.56 (s, 1H), 1.45 (s, 1H). Ms (M$^+$+1): 286.

Example 17

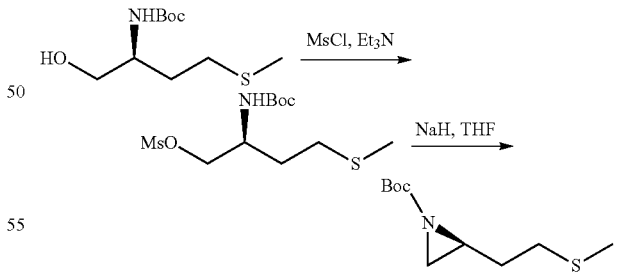

Into a 250 mL three-necked flask were added the starting compound as shown in the above route (4.7 g, 0.02 mol), dichloromethane (60 mL) and triethylamine (3.03 g, 0.03 mol). MsCl (3.15 g, 0.03 mol) was slowly added dropwise at 0° C. After addition, the mixture was warmed to room temperature and stirred for 4 h. Then, 60 mL 1N dilute hydrochloric acid was added to quench the reaction. Upon standing, the organic layer was separated and washed with 50 mL saturated solution of sodium chloride, followed by drying, filtration and concentration. The obtained crude product was directly used in the next step without purification.

The intermediate obtained from the above reaction was dissolved in 50 mL anhydrous tetrahydrofuran under nitrogen. Into this solution was added 60% sodium hydride (0.8 g, 0.02 mol) in portions at 0° C. After reacting for 15 min under agitation, 50 mL saturated solution of ammonia chloride was added to quench the reaction. The aqueous layer was extracted with 50 mL ethyl acetate and the organic layer was washed with saturated solution of sodium chloride and then dried over anhydrous sodium sulfate, followed by filtration and concentration to obtain a crude product which was further treated by column chromatography to obtain a product as a viscous liquid (3.7 g). The total yield of the above two steps was 86%.

$^1$H NMR (400 MHz, CDCl$_3$) δ 2.80 (d, J=5.4 Hz, 2H), 2.49 (s, 1H), 2.38 (s, 3H), 2.16 (s, 1H), 2.04 (s, 2H), 1.51 (d, J=4.9 Hz, 10H). $^{13}$C NMR (400 Hz, CDCl$_3$) δ 162.31, 80.95, 36.99, 32.02, 31.59, 31.43, 27.84, 15.50. Ms (M$^+$+1): 218.

Example 18

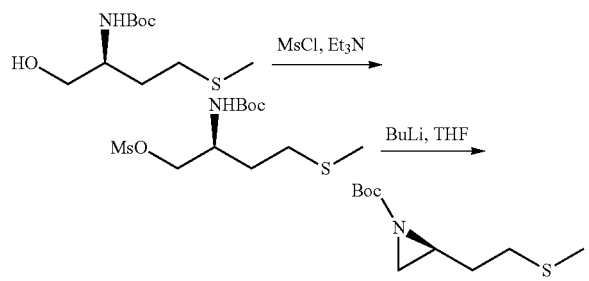

Into a 250 mL three-necked flask were added the starting compound as shown in the above route (4.7 g, 0.02 mol), dichloromethane (60 mL) and triethylamine (3.03 g, 0.03 mol). MsCl (3.15 g, 0.03 mol) was slowly added dropwise at 0° C. After addition, the mixture was warmed to room temperature and stirred for 4 h. Then, 60 mL 1N dilute hydrochloric acid was added to quench the reaction. Upon standing, the separated organic layer was washed with 50 mL saturated solution of sodium chloride, followed by drying, filtration and concentration. The obtained crude product was directly used in the next step without purification.

The intermediate obtained from the above reaction was dissolved in 50 mL anhydrous tetrahydrofuran under nitrogen. Into this solution was added dropwise 2.5M butyl lithium (10 mL, 0.025 mol) at −10° C. After reacting for 30 min under agitation, 50 mL saturated solution of ammonia chloride was added to quench the reaction. The aqueous layer was extracted with 50 mL ethyl acetate and the organic layer was washed with saturated solution of sodium chloride and then dried over anhydrous sodium sulfate, followed by filtration and concentration to obtain a crude product which was further treated by column chromatography to obtain a product as a viscous liquid (3.9 g). The total yield of the above two steps was 90%.

$^1$H NMR (400 MHz, CDCl$_3$) δ 2.80 (d, J=5.4 Hz, 2H), 2.49 (s, 1H), 2.38 (s, 3H), 2.16 (s, 1H), 2.04 (s, 2H), 1.51 (d, J=4.9 Hz, 10H). $^{13}$C NMR (400 Hz, CDCl$_3$) δ 162.31, 80.95, 36.99, 32.02, 31.59, 31.43, 27.84, 15.50. Ms (M$^+$+1): 218.

Example 19

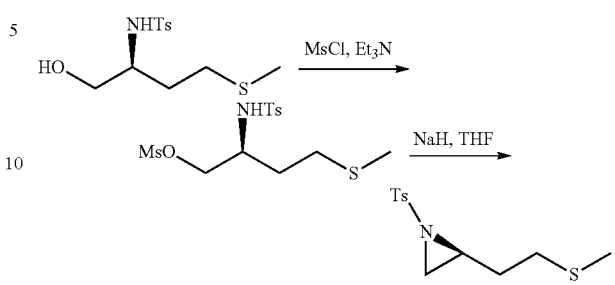

Into a 250 mL three-necked flask were added the starting compound as shown in the above route (5.8 g, 0.02 mol), dichloromethane (60 mL) and triethylamine (3.03 g, 0.03 mol). MsCl (3.15 g, 0.03 mol) was slowly added dropwise at 0° C. After addition, the mixture was warmed to room temperature and stirred for 4 h. Then, 60 mL 1N dilute hydrochloric acid was added to quench the reaction. Upon standing, the separated organic layer was washed with 50 mL saturated solution of sodium chloride, followed by drying, filtration and concentration. The obtained crude product was directly used in the next step without purification.

The intermediate obtained from the above reaction was dissolved in 50 mL anhydrous tetrahydrofuran under nitrogen. Into this solution was added 60% sodium hydride (0.8 g, 0.02 mol) in portions at 0° C. After reacting for 15 min under agitation, 50 mL saturated solution of ammonia chloride was added to quench the reaction. The aqueous layer was extracted with 50 mL ethyl acetate and the organic layer was washed with saturated solution of sodium chloride and then dried over anhydrous sodium sulfate, followed by filtration and concentration to obtain a crude product which was further treated by column chromatography to obtain a product as a viscous liquid (4.3 g). The total yield of the above two steps was 80%.

$^1$H NMR (400 MHz, CDCl$_3$) δ 8.10~7.35 (m, 5H), 2.80 (d, J=5.4 Hz, 2H), 2.49 (s, 1H), 2.38 (s, 3H), 2.35 (s, 3H), 2.16 (s, 1H), 2.04 (s, 2H), 1.51 (s, 1H). Ms (M$^+$+1): 272.

Example 20

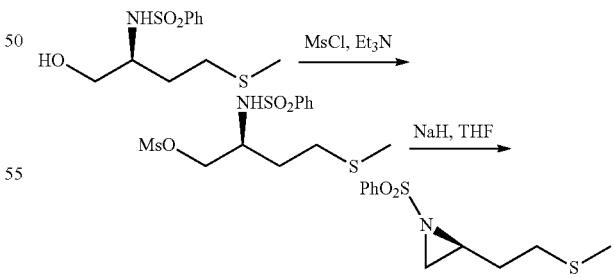

Into a 250 mL three-necked flask were added the starting compound as shown in the above route (5.5 g, 0.02 mol), dichloromethane (60 mL) and triethylamine (3.03 g, 0.03 mol). MsCl (3.15 g, 0.03 mol) was slowly added dropwise at 0° C. After addition, the mixture was warmed to room temperature and stirred for 4 h. Then, 60 mL 1N dilute hydrochloric acid was added to quench the reaction. Upon standing, the separated organic layer was washed with 50 mL saturated solution of sodium chloride, followed by drying, filtration and concentration. The obtained crude product was directly used in the next step without purification.

The intermediate obtained from the above reaction was dissolved in 50 mL anhydrous tetrahydrofuran under nitrogen. Into this solution was added 60% sodium hydride (0.8 g, 0.02 mol) in portions at 0° C. After reacting for 15 min under agitation, 50 mL saturated solution of ammonia chloride was added to quench the reaction. The aqueous layer was extracted with 50 mL ethyl acetate and the organic layer was washed with saturated solution of sodium chloride and then dried over anhydrous sodium sulfate, followed by filtration and concentration to obtain a crude product which was further treated by column chromatography to obtain a product as a viscous liquid (3.9 g). The total yield of the above two steps was 76%.

$^1$H NMR (400 MHz, CDCl$_3$) δ 8.10~7.35 (m, 5H), 2.80 (d, J=5.4 Hz, 2H), 2.49 (s, 1H), 2.38 (s, 3H), 2.16 (s, 1H), 2.04 (s, 2H), 1.51 (s, 1H). Ms (M$^+$+1): 258.

Example 21

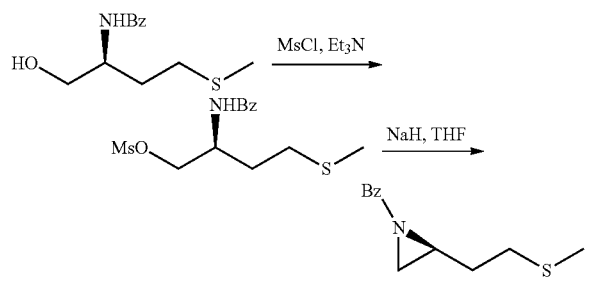

Into a 250 mL three-necked flask were added the starting compound as shown in the above route (4.78 g, 0.02 mol), dichloromethane (60 mL) and triethylamine (3.03 g, 0.03 mol). MsCl (3.15 g, 0.03 mol) was slowly added dropwise at 0° C. After addition, the mixture was warmed to room temperature and stirred for 4 h. Then, 60 mL 1N dilute hydrochloric acid was added to quench the reaction. Upon standing, the separated organic layer was washed with 50 mL saturated solution of sodium chloride, followed by drying, filtration and concentration. The obtained crude product was directly used in the next step without purification.

The intermediate obtained from the above reaction was dissolved in 50 mL anhydrous tetrahydrofuran under nitrogen. Into this solution was added 60% sodium hydride (0.8 g, 0.02 mol) in portions at 0° C. After reacting for 15 min under agitation, 50 mL saturated solution of ammonia chloride was added to quench the reaction. The aqueous layer was extracted with 50 mL ethyl acetate and the organic layer was washed with saturated solution of sodium chloride and then dried over anhydrous sodium sulfate, followed by filtration and concentration to obtain a crude product which was further treated by column chromatography to obtain a product as a viscous liquid (2.5 g). The total yield of the above two steps was 57%.

$^1$H NMR (400 MHz, CDCl$_3$) δ 7.80~7.25 (m, 5H), 2.80 (d, J=5.4 Hz, 2H), 2.49 (s, 1H), 2.38 (s, 3H), 2.16 (s, 1H), 2.04 (s, 2H), 1.51 (d, J=4.9 Hz, 1H). Ms (M$^+$+1): 222.

Example 22

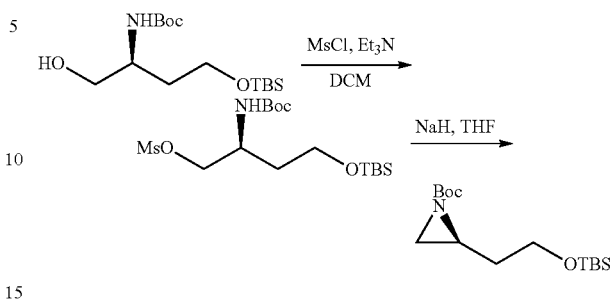

Into a 250 mL three-necked flask were added the starting compound as shown in the above route (6.38 g, 0.02 mol), dichloromethane (60 mL) and triethylamine (3.03 g, 0.03 mol). MsCl (3.15 g, 0.03 mol) was slowly added dropwise at 0° C. After addition, the mixture was warmed to room temperature and stirred for 4 h. Then, 60 mL 1N dilute hydrochloric acid was added to quench the reaction. Upon standing, the separated organic layer was washed with 50 mL saturated solution of sodium chloride, followed by drying, filtration and concentration. The obtained crude product was directly used in the next step without purification.

The intermediate obtained from the above reaction was dissolved in 50 mL anhydrous tetrahydrofuran under nitrogen. Into this solution was added 60% sodium hydride (0.8 g, 0.02 mol) in portions at 0° C. After reacting for 15 min under agitation, 50 mL saturated solution of ammonia chloride was added to quench the reaction. The aqueous layer was extracted with 50 mL ethyl acetate and the organic layer was washed with saturated solution of sodium chloride and then dried over anhydrous sodium sulfate, followed by filtration and concentration to obtain a crude product which was further treated by column chromatography to obtain a product as a viscous liquid (4.3 g). The total yield of the above two steps was 73%.

$^1$H NMR (500 MHz, CDCl$_3$) δ 3.95~3.63 (m, 2H), 2.61~2.43 (m, 1H), 2.28 (d, J=6.1 Hz, 1H), 1.96 (d, J=3.8 Hz, 1H), 1.86~1.72 (m, 1H), 1.72~1.55 (m, 1H), 1.46 (s, 6H), 0.93 (s, 9H), 0.07 (d, J=1.8 Hz, 6H). $^{13}$C NMR (CDCl$_3$) δ 162.47, 80.84, 60.12, 35.52, 35.41, 31.40, 28.30, 27.86, 27.81, 22.75, −0.58. Ms (M$^+$+1): 302.

Example 23

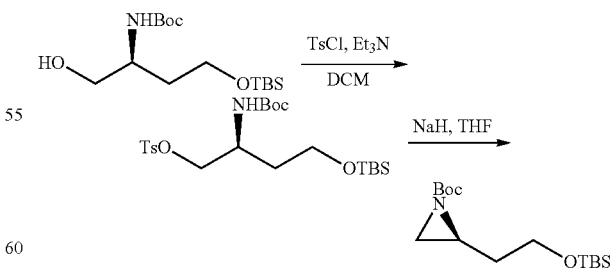

Into a 250 mL three-necked flask were added the starting compound as shown in the above route (6.38 g, 0.02 mol), dichloromethane (60 mL) and triethylamine (3.03 g, 0.03 mol). TsCl (5.7 g, 0.03 mol) was slowly added dropwise at 0° C. After addition, the mixture was warmed to room temperature and stirred for 4 h. Then, 60 mL 1N dilute hydrochloric acid was added to quench the reaction. Upon standing, the separated organic layer was washed with 50 mL saturated solution of sodium chloride, followed by drying, filtration and concentration. The obtained crude product was directly used in the next step without purification.

The intermediate obtained from the above reaction was dissolved in 50 mL anhydrous tetrahydrofuran under nitrogen. Into this solution was added 60% sodium hydride (0.8 g, 0.02 mol) in portions at 0° C. After reacting for 15 min under agitation, 50 mL saturated solution of ammonia chloride was added to quench the reaction. The aqueous layer was extracted with 50 mL ethyl acetate and the organic layer was washed with saturated solution of sodium chloride and then dried over anhydrous sodium sulfate, followed by filtration and concentration to obtain a crude product which was further treated by column chromatography to obtain a product as a viscous liquid (4.6 g). The total yield of the above two steps was 78%.

$^1$H NMR (500 MHz, CDCl$_3$) δ 3.95~3.63 (m, 2H), 2.61~2.43 (m, 1H), 2.28 (d, J=6.1 Hz, 1H), 1.96 (d, J=3.8 Hz, 1H), 1.86~1.72 (m, 1H), 1.72~1.55 (m, 1H), 1.46 (s, 6H), 0.93 (s, 9H), 0.07 (d, J=1.8 Hz, 6H). $^{13}$C NMR (CDCl$_3$) δ 162.47, 80.84, 60.12, 35.52, 35.41, 31.40, 28.30, 27.86, 27.81, 22.75, −0.58. Ms (M$^+$+1): 302.

Example 24

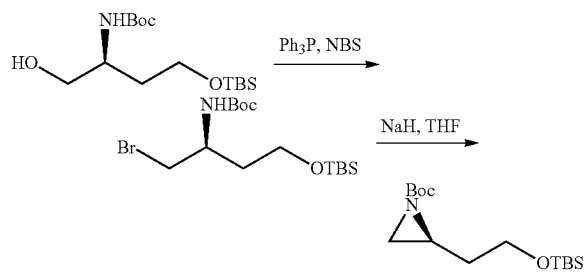

Into a 250 mL three-necked flask were added the starting compound as shown in the above route (6.38 g, 0.02 mol) and dichloromethane (60 mL). Triphenylphosphine (7.86 g, 0.03 mol) and NBS (5.34 g, 0.03 mol) were slowly added dropwise at 0° C. After addition, the mixture was warmed to room temperature and stirred for 4 h. Then, 60 mL 1N water was added to quench the reaction. Upon standing, the organic layer was separated and washed with 50 mL saturated solution of sodium chloride, followed by drying, filtration and concentration. The obtained crude product was directly used in the next step without purification.

The intermediate obtained from the above reaction was dissolved in 50 mL anhydrous tetrahydrofuran under nitrogen. Into this solution was added 60% sodium hydride (0.8 g, 0.02 mol) in portions at 0° C. After reacting for 15 min under agitation, 50 mL saturated solution of ammonia chloride was added to quench the reaction. The aqueous layer was extracted with 50 mL ethyl acetate and the organic layer was washed with saturated solution of sodium chloride and then dried over anhydrous sodium sulfate, followed by filtration and concentration to obtain a crude product which was further treated by column chromatography to obtain a product as a viscous liquid (3.83 g). The total yield of the above two steps was 65%.

$^1$H NMR (500 MHz, CDCl$_3$) δ 3.95~3.63 (m, 2H), 2.61~2.43 (m, 1H), 2.28 (d, J=6.1 Hz, 1H), 1.96 (d, J=3.8 Hz, 1H), 1.86~1.72 (m, 1H), 1.72~1.55 (m, 1H), 1.46 (s, 6H), 0.93 (s, 9H), 0.07 (d, J=1.8 Hz, 6H). $^{13}$C NMR (CDCl$_3$) δ 162.47, 80.84, 60.12, 35.52, 35.41, 31.40, 28.30, 27.86, 27.81, 22.75, −0.58. Ms (M$^+$+1): 302.

Example 25

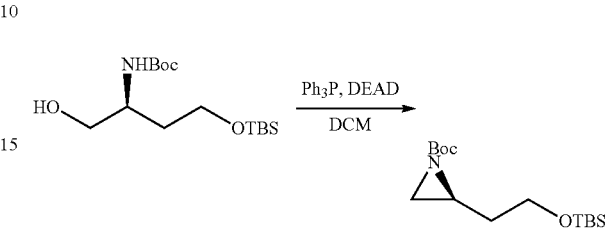

Into a 250 mL three-necked flask were added the starting compound as shown in the above route (6.38 g, 0.02 mol) and 60 mL dried tetrahydrofuran under nitrogen. Triphenylphosphine (7.86 g, 0.03 mol) was added slowly at 0° C., followed by the addition of diazenedi(diethylcarbonate) DEAD (5.22 g, 0.03 mol). After reacting for 10 h at room temperature under agitation, the reaction mixture was concentrated under reduced pressure. To the obtained residue was added 10 mL tetrahydrofuran. After heating under agitation, the residue was dissolved. n-Hexane was then added dropwise to the mixture till white solid was precipitated. The reactants were cooled down and then filtered. The obtained filtrate was concentrated to obtain a product as a viscous liquid (3.65 g) by column chromatography. The total yield of the above two steps was 61%.

$^1$H NMR (500 MHz, CDCl$_3$) δ 3.95~3.63 (m, 2H), 2.61~2.43 (m, 1H), 2.28 (d, J=6.1 Hz, 1H), 1.96 (d, J=3.8 Hz, 1H), 1.86~1.72 (m, 1H), 1.72~1.55 (m, 1H), 1.46 (s, 6H), 0.93 (s, 9H), 0.07 (d, J=1.8 Hz, 6H). $^{13}$C NMR (CDCl$_3$) δ 162.47, 80.84, 60.12, 35.52, 35.41, 31.40, 28.30, 27.86, 27.81, 22.75, −0.58. Ms (M$^+$+1): 302.

Example 26

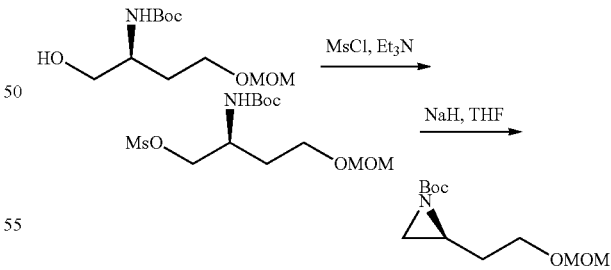

Into a 250 mL three-necked flask were added the starting compound as shown in the above route (4.98 g, 0.02 mol), dichloromethane (60 mL) and triethylamine (3.03 g, 0.03 mol). MsCl (3.15 g, 0.03 mol) was slowly added dropwise at 0° C. After addition, the mixture was warmed to room temperature and stirred for 4 h. Then, 60 mL 1N dilute hydrochloric acid was added to quench the reaction. Upon standing, the separated organic layer was washed with 50 mL saturated solution of sodium chloride, followed by drying, filtration and concentration. The obtained crude product was directly used in the next step without purification.

The intermediate obtained from the above reaction was dissolved in 50 mL anhydrous tetrahydrofuran under nitrogen. Into this solution was added 60% sodium hydride (0.8 g, 0.02 mol) in portions at 0° C. After reacting for 15 min under agitation, 50 mL saturated solution of ammonia chloride was added to quench the reaction. The aqueous layer was extracted with 50 mL ethyl acetate and the organic layer was washed with saturated solution of sodium chloride and then dried over anhydrous sodium sulfate, followed by filtration and concentration to obtain a crude product which was further treated by column chromatography to obtain a product as a viscous liquid (3.5 g). The total yield of the above two steps was 76%.

$^1$H NMR (400 MHz, CDCl$_3$) δ 4.50~4.47 (m, 2H), 3.60 (s, 2H), 3.41 (s, 3H), 2.49 (br, 1H), 2.12 (s, 1H), 1.84 (s, 2H), 1.51~1.47 (m, 10H). Ms (M$^+$+1): 232.

Example 27

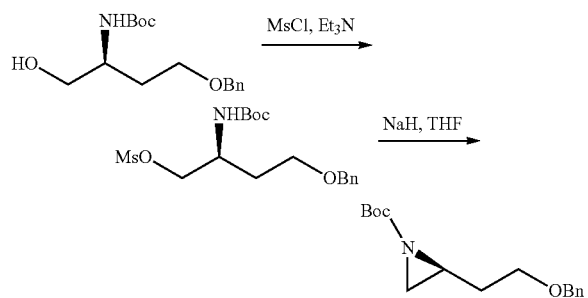

Into a 250 mL three-necked flask were added the starting compound as shown in the above route (5.9 g, 0.02 mol), dichloromethane (60 mL) and triethylamine (3.03 g, 0.03 mol). MsCl (3.15 g, 0.03 mol) was slowly added dropwise at 0° C. After addition, the mixture was warmed to room temperature and stirred for 4 h. Then, 60 mL 1N dilute hydrochloric acid was added to quench the reaction. Upon standing, the separated organic layer was washed with 50 mL saturated solution of sodium chloride, followed by drying, filtration and concentration. The obtained crude product was directly used in the next step without purification.

The intermediate obtained from the above reaction was dissolved in 50 mL anhydrous tetrahydrofuran under nitrogen. Into this solution was added 60% sodium hydride (0.8 g, 0.02 mol) in portions at 0° C. After reacting for 15 min under agitation, 50 mL saturated solution of ammonia chloride was added to quench the reaction. The aqueous layer was extracted with 50 mL ethyl acetate and the organic layer was washed with saturated solution of sodium chloride and then dried over anhydrous sodium sulfate, followed by filtration and concentration to obtain a crude product which was further treated by column chromatography to obtain a product as a viscous liquid (4.4 g). The total yield of the above two steps was 80%.

$^1$H NMR (400 MHz, CDCl$_3$) δ 7.30 (dt, J=1.3, 0.6 Hz, 5H), 4.79 (s, 2H), 3.56 (s, 2H), 2.52 (s, 1H), 2.16 (s, 1H), 1.84 (s, 2H), 1.51 (d, J=2.1 Hz, 10H). Ms (M$^+$+1): 278.

Example 28

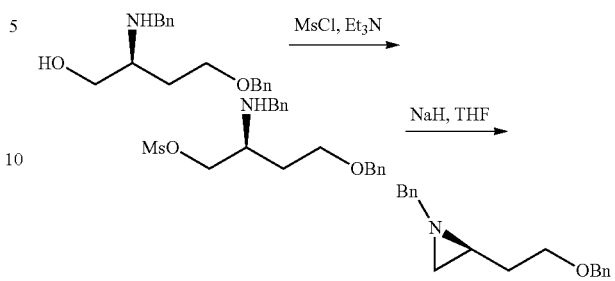

Into a 250 mL three-necked flask were added the starting compound as shown in the above route (5.7 g, 0.02 mol), dichloromethane (60 mL) and triethylamine (3.03 g, 0.03 mol). MsCl (3.15 g, 0.03 mol) was slowly added dropwise at 0° C. After addition, the mixture was warmed to room temperature and stirred for 4 h. Then, 60 mL 1N dilute hydrochloric acid was added to quench the reaction. Upon standing, the separated organic layer was washed with 50 mL saturated solution of sodium chloride, followed by drying, filtration and concentration. The obtained crude product was directly used in the next step without purification.

The intermediate obtained from the above reaction was dissolved in 50 mL anhydrous tetrahydrofuran under nitrogen. Into this solution was added 60% sodium hydride (0.8 g, 0.02 mol) in portions at 0° C. After reacting for 15 min under agitation, 50 mL saturated solution of ammonia chloride was added to quench the reaction. The aqueous layer was extracted with 50 mL ethyl acetate and the organic layer was washed with saturated solution of sodium chloride and then dried over anhydrous sodium sulfate, followed by filtration and concentration to obtain a crude product which was further treated by column chromatography to obtain a product as a viscous liquid (4.4 g). The total yield of the above two steps was 83%.

$^1$H NMR (400 MHz, CDCl$_3$) δ 7.30~7.22 (m, 10H), 4.79 (s, 4H), 3.56 (s, 4H), 2.52 (s, 1H), 2.16 (s, 1H), 1.84 (s, 2H), 1.51 (s, 1H). Ms (M$^+$+1): 268.

Example 29

The starting compound as shown in the above route (6 g, 0.02 mol) was dissolved in 40 mL THF. To this mixture was added a solution of TBAF (7.3 g, 0.027 mol) in 40 mL THF. After reacting at room temperature for 2 h, 5 ml saturated solution of ammonia chloride was added to quench the reaction. The obtained solution was concentrated to recover THF. The residue was extracted with 50 mL ethyl acetate. The obtained organic layer was washed with saturated solution of sodium chloride and then dried over anhydrous sodium sulfate, followed by filtration and concentration to obtain a crude product which was further treated by column chromatography to obtain a product as a viscous liquid (3.4 g, yield 92%).

$^1$H NMR (500 MHz, CDCl$_3$) δ 3.74 (s, 2H), 3.15 (s, 1H), 2.41 (d, J=5.9 Hz, 1H), 2.26 (d, J=6.1 Hz, 1H), 1.93 (d, J=3.4

Hz, 1H), 1.90~1.78 (m, 1H), 1.54~1.42 (m, 1H), 1.38 (s, 9H).
$^{13}$C NMR (CDCl$_3$) δ 162.55, 81.55, 60.54, 35.96, 34.35, 31.06, 28.31, 28.27, 27.85. Ms (M$^+$+1): 188.

Example 30

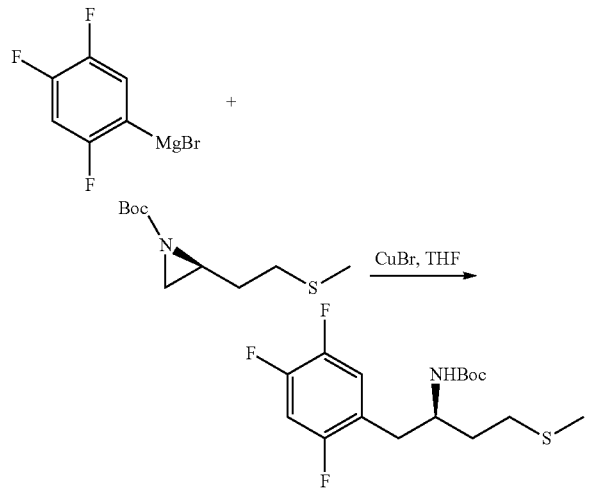

Into a 100 mL three-necked flask were added 4.62 g 1-bromo-2,4,5-trifluorobenzene (0.022 mol) and anhydrous tetrahydrofuran (50 mL). The resulting mixture was cooled to −20° C. The solution of isopropylmagnesium bromide (22 mmol) in tetrahydrofuran (22 ml, 1M THF) was slowly added dropwise under nitrogen. After the addition was completed, the reactants were maintained at −20° C. for later use.

Cuprous bromide-dimethyl sulfide (0.41 g, 0.002 mol) was suspended in 5 ml anhydrous tetrahydrofuran. The resulting mixture was cooled to −5° C. The Grignard reagent as obtained above was slowly added dropwise under nitrogen. After 15 min, a solution of the aziridine compound as shown in the above reaction formula (3.26 g, 0.015 mol) in 30 mL tetrahydrofuran was slowly added dropwise. After additional 5 min, 50 mL saturated solution of ammonia chloride was added to quench the reaction. Into this obtained solution was added 50 mL ethyl acetate for an extraction. The separated water layer was extracted with another 50 mL ethyl acetate. The obtained organic layers were collected together and further washed with saturated solution of sodium chloride and then dried over anhydrous sodium sulfate, followed by filtration and concentration to obtain a crude product which was further treated by column chromatography to obtain a compound (4.29 g, yield 82%).

$^1$H NMR (400 MHz, CDCl$_3$) δ 7.15~6.94 (m, 1H), 6.88 (d, J=6.8 Hz, 1H), 4.47 (d, J=8.9 Hz, 1H), 4.00~3.80 (m, 1H), 2.92~2.76 (m, 1H), 2.76~2.64 (m, 1H), 2.64~2.44 (m, 2H), 2.06 (d, J=14.6 Hz, 3H), 1.84 (s, 1H), 1.66 (qd, J=14.0, 8.0 Hz, 1H), 1.47~1.31 (m, 9H). Ms (M$^+$+1): 350.

Example 31

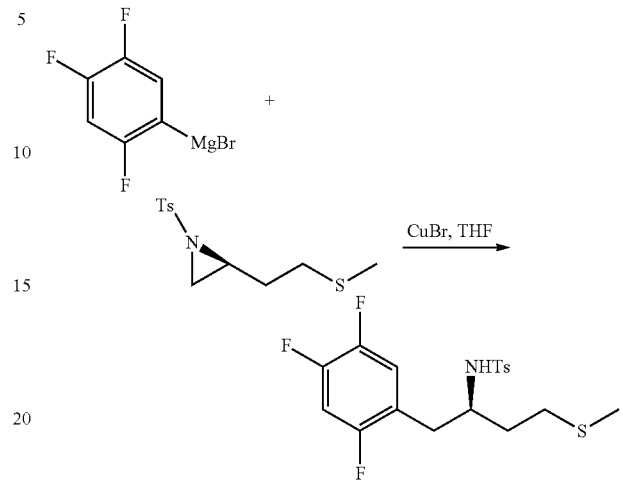

Into a 100 mL three-necked flask were added 4.62 g 1-bromo-2,4,5-trifluorobenzene (0.022 mol) and anhydrous tetrahydrofuran (50 mL). The resulting mixture was cooled to −20° C. The solution of isopropylmagnesium bromide (22 mmol) in tetrahydrofuran (22 ml, 1M THF) was slowly added dropwise under nitrogen. After the addition was complete, the reactants were maintained at −20° C. for later use.

Cuprous bromide-dimethyl sulfide (0.41 g, 0.002 mol) was suspended in 5 ml anhydrous tetrahydrofuran. The resulting mixture was cooled to −5° C. The Grignard reagent as obtained above was slowly added dropwise under nitrogen. After 15 min, a solution of the aziridine compound as shown in the above reaction formula (4.1 g, 0.015 mol) in 30 mL tetrahydrofuran was slowly added dropwise. After additional 5 min, 50 mL saturated solution of ammonia chloride was added to quench the reaction. Into this obtained solution was added 50 mL ethyl acetate. The separated water layer was extracted with another 50 mL ethyl acetate. The obtained organic layers were collected together and further washed with saturated solution of sodium chloride and then dried over anhydrous sodium sulfate, followed by filtration and concentration to obtain a crude product which was further treated by column chromatography to obtain a compound (5.26 g, yield 87%).

$^1$H NMR (400 MHz, CDCl$_3$) δ 7.87~7.61 (m, 5H), 7.15~6.94 (m, 1H), 6.88 (d, J=6.8 Hz, 1H), 5.02 (d, J=8.9 Hz, 1H), 4.00~3.80 (m, 1H), 2.92~2.76 (m, 1H), 2.76~2.64 (m, 1H), 2.64~2.44 (m, 2H), 2.06 (d, J=14.6 Hz, 3H), 1.84 (s, 1H), 1.62 (s, 1H). Ms (M$^+$+1): 404.

Example 32

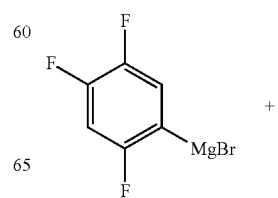

-continued

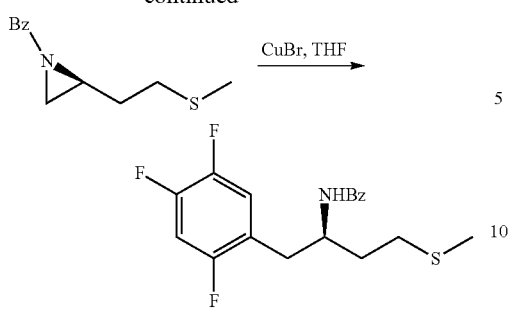
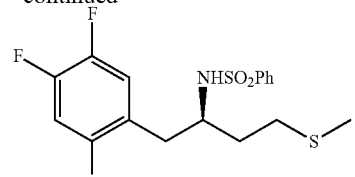

Into a 100 mL three-necked flask were added 4.62 g 1-bromo-2,4,5-trifluorobenzene (0.022 mol) and anhydrous tetrahydrofuran (50 mL). The resulting mixture was cooled to −20° C. The solution of isopropylmagnesium bromide (22 mmol) in tetrahydrofuran (22 ml, 1M THF) was slowly added dropwise under nitrogen. After the addition was complete, the reactants were maintained at −20° C. for later use.

Cuprous bromide-dimethyl sulfide (0.41 g, 0.002 mol) was suspended in 5 ml anhydrous tetrahydrofuran. The resulting mixture was cooled to −5° C. The Grignard reagent as obtained above was slowly added dropwise under nitrogen. After 15 min, a solution of the aziridine compound as shown in the above reaction formula (4.16 g, 0.015 mol) in 30 mL tetrahydrofuran was slowly added dropwise. After additional 5 min, 50 mL saturated solution of ammonia chloride was added to quench the reaction. Into this obtained solution was added 50 mL ethyl acetate. The separated water layer was extracted with another 50 mL ethyl acetate. The obtained organic layers were collected together and further washed with saturated solution of sodium chloride and then dried over anhydrous sodium sulfate, followed by filtration and concentration to obtain a crude product, which was further treated by column chromatography to obtain a compound (5.26 g, 0.0116 mol, yield 77%).

$^1$H NMR (400 MHz, CDCl$_3$) δ 8.10 (d, J=5.4 Hz, 2H), 7.72~7.66 (m, 3H), 7.15~6.94 (m, 1H), 6.88 (d, J=6.8 Hz, 1H), 4.47 (d, J=8.9 Hz, 1H), 4.00~3.80 (m, 1H), 2.92~2.76 (m, 1H), 2.76~2.64 (m, 1H), 2.64~2.44 (m, 2H), 2.06 (d, J=14.6 Hz, 3H), 1.84 (s, 1H), 1.66 (qd, J=14.0, 8.0 Hz, 1H). Ms (M$^+$+1): 354.

Example 33

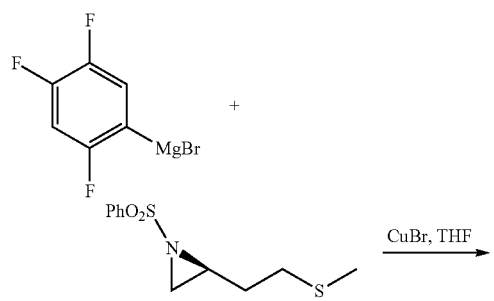

Into a 100 mL three-necked flask were added 4.62 g 1-bromo-2,4,5-trifluorobenzene (0.022 mol) and anhydrous tetrahydrofuran (50 mL). The resulting mixture was cooled to −20° C. The solution of isopropylmagnesium bromide (22 mmol) in tetrahydrofuran (22 ml, 1M THF) was slowly added dropwise under nitrogen. After the addition was complete, the reactants were maintained at −20° C. for later use.

Cuprous bromide-dimethyl sulfide (0.41 g, 0.002 mol) was suspended in 5 ml anhydrous tetrahydrofuran. The resulting mixture was cooled to −5° C. The Grignard reagent as described above was slowly added dropwise under nitrogen. After 15 min, a solution of the aziridine compound as shown in the above reaction formula (4.16 g, 0.015 mol) in 30 mL tetrahydrofuran was slowly added dropwise. After additional 5 min, 50 mL saturated solution of ammonia chloride was added to quench the reaction. Into this obtained solution was added 50 mL ethyl acetate. The separated water layer was extracted with another 50 mL ethyl acetate. The obtained organic layers were collected together and further was washed with saturated solution of sodium chloride and then dried over anhydrous sodium sulfate, followed by filtration and concentration to obtain a crude product, which was further treated by column chromatography to obtain a compound (4.98 g, 0.0128 mol, yield 85%).

$^1$H NMR (400 MHz, CDCl$_3$) δ 7.87~7.61 (m, 5H), 7.15~6.94 (m, 1H), 6.88 (d, J=6.8 Hz, 1H), 5.02 (d, J=8.9 Hz, 1H), 4.00-3.80 (m, 1H), 2.92~2.76 (m, 1H), 2.76~2.64 (m, 1H), 2.64~2.44 (m, 2H), 2.06 (d, J=14.6 Hz, 3H), 1.84 (s, 1H), 1.62 (s, 1H). Ms (M$^+$+1): 390.

Example 34

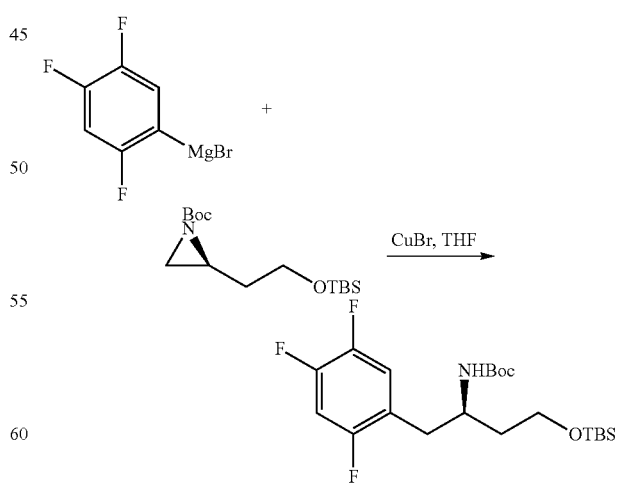

Into a 100 mL three-necked flask were added 4.62 g 1-bromo-2,4,5-trifluorobenzene (0.022 mol) and anhydrous tetrahydrofuran (50 mL). The resulting mixture was cooled to −20° C. The solution of isopropylmagnesium bromide (22 mmol) in tetrahydrofuran (22 ml, 1M THF) was slowly added dropwise under nitrogen. After the addition was complete, the reactants were maintained at −20° C. for later use.

Cuprous bromide-dimethyl sulfide (0.41 g, 0.002 mol) was suspended in 5 ml anhydrous tetrahydrofuran. The resulting mixture was cooled to −5° C. The Grignard reagent as described above was slowly added dropwise under nitrogen. After 15 min, a solution of the aziridine compound as shown in the above reaction formula (4.54 g, 0.015 mol) in 30 mL tetrahydrofuran was slowly added dropwise. After additional 5 min, 50 mL saturated solution of ammonia chloride was added to quench the reaction. Into this obtained solution was added 50 mL ethyl acetate. The separated water layer was extracted with another 50 mL ethyl acetate. The obtained organic layers were collected together and further washed with saturated solution of sodium chloride and then dried over anhydrous sodium sulfate, followed by filtration and concentration to obtain a crude product, which was further treated by column chromatography to obtain a compound (5.07 g, 0.012 mol, yield 78%).

$^1$H NMR (400 MHz, CDCl$_3$) δ 7.03 (t, J=10.5 Hz, 1H), 6.91 (t, J=10.7 Hz, 1H), 5.14 (d, J=12.6 Hz, 1H), 3.97~3.85 (m, 1H), 3.82 (d, J=6.2 Hz, 1H), 3.77~3.55 (m, 1H), 2.82 (s, 2H), 1.87~1.68 (m, 1H), 1.63~1.48 (m, 1H), 1.39 (s, 9H), 0.91 (s, 9H), 0.06 (d, J=4.6 Hz, 6H). Ms (M$^+$+1): 434.

Example 35

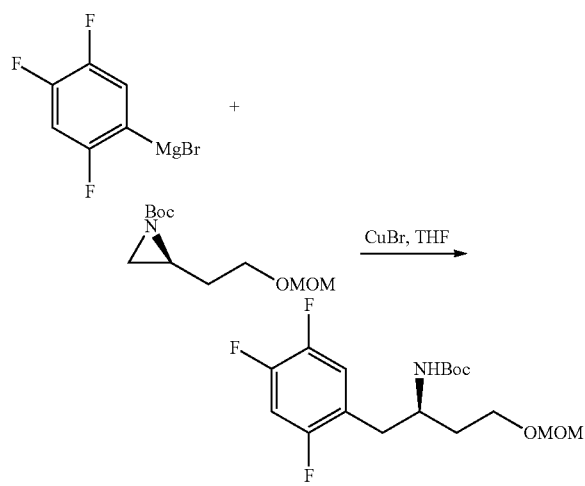

Into a 100 mL three-necked flask were added 4.62 g 1-bromo-2,4,5-trifluorobenzene (0.022 mol) and anhydrous tetrahydrofuran (50 mL). The resulting mixture was cooled to −20° C. The solution of isopropylmagnesium bromide (22 mmol) in tetrahydrofuran (22 ml, 1M THF) was slowly added dropwise under nitrogen. After the addition was complete, the reactants were maintained at −20° C. for later use.

Cuprous bromide-dimethyl sulfide (0.41 g, 0.002 mol) was suspended in 5 ml anhydrous tetrahydrofuran. The resulting mixture was cooled to −5° C. The Grignard reagent as described above was slowly added dropwise under nitrogen. After 15 min, a solution of the aziridine compound as shown in the above reaction formula (3.46 g, 0.015 mol) in 30 mL tetrahydrofuran was slowly added dropwise. After additional 5 min, 50 mL saturated solution of ammonia chloride was added to quench the reaction. Into this obtained solution was added 50 mL ethyl acetate. The separated water layer was extracted with another 50 mL ethyl acetate. The obtained organic layers were collected together and further washed with saturated solution of sodium chloride and then dried over anhydrous sodium sulfate, followed by filtration and concentration to obtain a crude product, which was further treated by column chromatography to obtain a compound (3.98 g, 0.011 mol, yield 73%).

$^1$H NMR (400 MHz, CDCl$_3$) δ 7.01 (t, J=10.5 Hz, 1H), 6.92~6.88 (m, 1H), 5.14 (d, J=12.6 Hz, 1H), 4.50 (s, 2H), 3.95~3.85 (m, 1H), 3.82~3.77 (m, 1H), 3.77~3.55 (m, 1H), 3.40 (s, 3H), 2.82 (s, 2H), 1.87~1.68 (m, 1H), 1.63~1.48 (m, 1H), 1.39 (s, 9H). Ms (M$^+$+1): 364.

Example 36

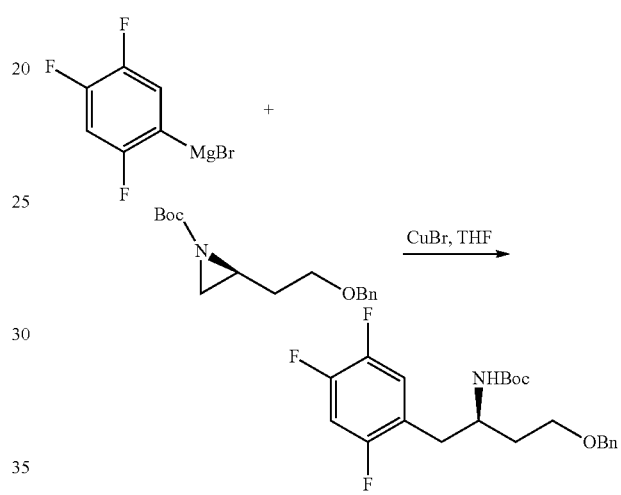

Into a 100 mL three-necked flask were added 4.62 g 1-bromo-2,4,5-trifluorobenzene (0.022 mol) and anhydrous tetrahydrofuran (50 mL). The resulting mixture was cooled to −20° C. The solution of isopropylmagnesium bromide (22 mmol) in tetrahydrofuran (22 ml, 1M THF) was slowly added dropwise under nitrogen. After the addition was complete, the reactants were maintained at −20° C. for later use.

Cuprous bromide-dimethyl sulfide (0.41 g, 0.002 mol) was suspended in 5 ml anhydrous tetrahydrofuran. The resulting mixture was cooled to −5° C. The Grignard reagent as described above was slowly added dropwise under nitrogen. After 15 min, a solution of the aziridine compound as shown in the above reaction formula (4.16 g, 0.015 mol) in 30 mL tetrahydrofuran was slowly added dropwise. After additional 5 min, 50 mL saturated solution of ammonia chloride was added to quench the reaction. Into this obtained solution was added 50 mL ethyl acetate. The separated water layer was extracted with another 50 mL ethyl acetate. The obtained organic layers were collected together and further washed with saturated solution of sodium chloride and then dried over anhydrous sodium sulfate, followed by filtration and concentration to obtain a crude product, which was further treated by column chromatography to obtain a compound (5.41 g, 0.0132 mol, yield 88%).

$^1$H NMR (400 MHz, CDCl$_3$) δ7.53~7.22 (m, 5H), 7.05 (t, J=10.5 Hz, 1H), 6.93 (t, J=10.7 Hz, 1H), 5.12 (d, J=12.6 Hz, 1H), 3.97~3.85 (m, 1H), 3.82 (d, J=6.2 Hz, 1H), 3.77~3.55 (m, 1H), 3.51 (s, 2H), 2.82 (s, 2H), 1.87~1.68 (m, 1H), 1.63~1.48 (m, 1H), 1.39 (s, 9H). Ms (M$^+$+1): 410.

Example 37

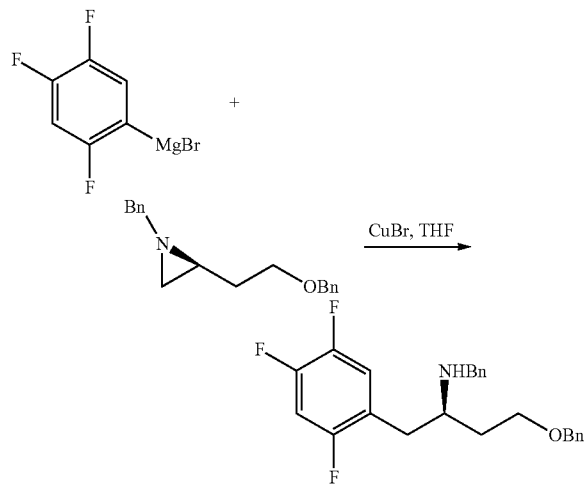

Into a 100 mL three-necked flask were added 4.62 g 1-bromo-2,4,5-trifluorobenzene (0.022 mol) and anhydrous tetrahydrofuran (50 mL). The resulting mixture was cooled to −20° C. The solution of isopropylmagnesium bromide (22 mmol) in tetrahydrofuran (22 ml, 1M THF) was slowly added dropwise under nitrogen. After the addition was complete, the reactants were maintained at −20° C. for later use.

Cuprous bromide-dimethyl sulfide (0.41 g, 0.002 mol) was suspended in 5 ml anhydrous tetrahydrofuran. The resulting mixture was cooled to −5° C. The Grignard reagent as described above was slowly added dropwise under nitrogen. After 15 min, a solution of the aziridine compound as shown in the above reaction formula (4.16 g, 0.015 mol) in 30 mL tetrahydrofuran was slowly added dropwise. After additional 5 min, 50 mL saturated solution of ammonia chloride was added to quench the reaction. Into this obtained solution was added 50 mL ethyl acetate. The separated water layer was extracted with another 50 mL ethyl acetate. The obtained organic layers were collected together and further washed with saturated solution of sodium chloride and then dried over anhydrous sodium sulfate, followed by filtration and concentration to obtain a crude product, which was further treated by column chromatography to obtain a compound (4.08 g, 0.0116 mol, yield 77%).

$^1$H NMR (400 MHz, CDCl$_3$) δ7.53~7.22 (m, 10H), 7.05 (t, J=10.5 Hz, 1H), 6.93 (t, J=10.7 Hz, 1H), 5.12 (d, J=12.6 Hz, 1H), 3.97~3.85 (m, 1H), 3.82 (d, J=6.2 Hz, 1H), 3.77~3.55 (m, 1H), 3.62 (s, 2H), 3.51 (s, 2H), 2.82 (s, 2H), 1.87~1.68 (m, 1H), 1.63~1.48 (m, 1H). Ms (M$^+$+1): 400.

Example 38

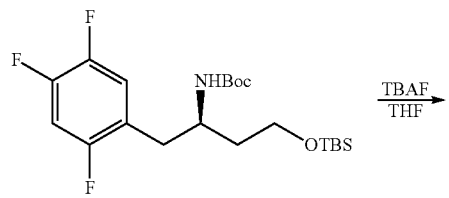

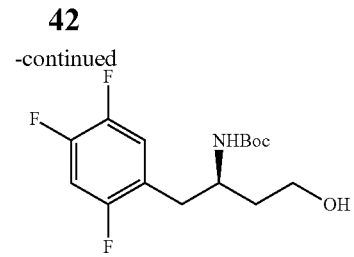

Into a three-necked flask were added the raw material as shown in the above reaction formula (5.07 g, 0.012 mol) and tetrahydrofuran (50 mL). At room temperature, tetrabutyl ammonium fluoride (3.92 g, 0.015 mol) was then added and the mixture was stirred for 2 h. The solvent was removed by distillation. Then 50 mL dichloromethane and 50 mL water were added. After separation, the organic layer was washed with dilute hydrochloric acid and saturated solution of sodium hydrogen carbonate separately, and then dried over anhydrous sodium sulfate, followed by filtration and concentration to obtain a crude product (3.64 g, 95%).

$^1$H NMR (500 MHz, CDCl$_3$) δ 7.05 (d, J=8.3 Hz, 1H), 6.91 (d, J=6.6 Hz, 1H), 4.56 (d, J=9.0 Hz, 1H), 4.13~3.96 (m, 1H), 3.68 (d, J=6.0 Hz, 2H), 2.85~2.65 (m, 2H), 1.86 (dd, J=12.4, 7.7 Hz, 1H), 1.68 (s, 1H), 1.42 (s, 9H). Ms (M$^+$+1): 320.

Example 39

Into a three-necked flask were added the raw material as shown in the above reaction formula (3.98 g, 0.011 mol) and dichloromethane (50 mL). At room temperature, acetic acid (1.2 g, 0.02 mol) was then added and the mixture was stirred for 2 h. To the mixture were added 50 mL water. After separation of the layers, the organic layer was washed with saturated solution of sodium hydrogen carbonate and dilute hydrochloric acid separately, then dried over anhydrous sodium sulfate, followed by filtration and concentration to obtain a crude product (3.41 g, 97%).

$^1$H NMR (500 MHz, CDCl$_3$) δ 7.05 (d, J=8.3 Hz, 1H), 6.91 (d, J=6.6 Hz, 1H), 4.56 (d, J=9.0 Hz, 1H), 4.13~3.96 (m, 1H), 3.68 (d, J=6.0 Hz, 2H), 2.85~2.65 (m, 2H), 1.86 (dd, J=12.4, 7.7 Hz, 1H), 1.68 (s, 1H), 1.42 (s, 9H). Ms (M$^+$+1): 320.

Example 40

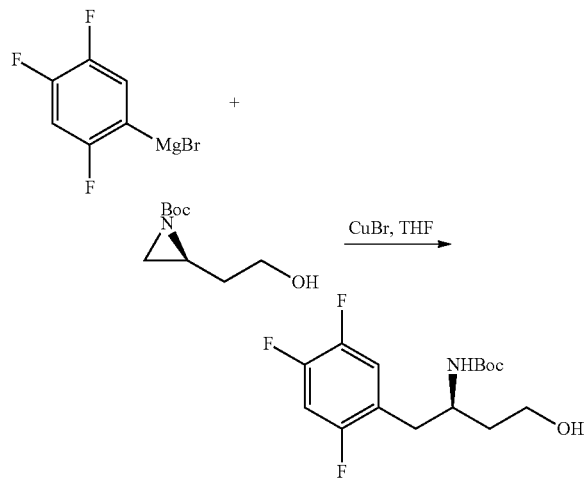

Into a 100 mL three-necked flask were added 4.62 g 1-bromo-2,4,5-trifluorobenzene (0.022 mol) and anhydrous tetrahydrofuran (50 mL). The resulting mixture was cooled to −20° C. The solution of isopropylmagnesium bromide (22 mmol) in tetrahydrofuran (22 ml, 1M THF) was slowly added dropwise under nitrogen. After the addition was complete, the reactants were maintained at −20° C. for later use.

Cuprous bromide-dimethyl sulfide (0.41 g, 0.002 mol) was suspended in 5 ml anhydrous tetrahydrofuran. The resulting mixture was cooled to −5° C. The Grignard reagent as described above was slowly added dropwise under nitrogen. After 15 min, a solution of the aziridine compound as shown in the above reaction formula (2.81 g, 0.015 mol) in 30 mL tetrahydrofuran was slowly added dropwise. After additional 5 min, 50 mL saturated solution of ammonia chloride was added to quench the reaction. Into this obtained solution was added 50 mL ethyl acetate. The separated water layer was extracted with another 50 mL ethyl acetate. The obtained organic layers were collected together and further washed with saturated solution of sodium chloride and then dried over anhydrous sodium sulfate, followed by filtration and concentration to obtain a crude product, which was further treated by column chromatography to obtain a compound (3.69 g, 0.0115 mol, yield 77%).

$^1$H NMR (500 MHz, CDCl$_3$) δ 7.05 (d, J=8.3 Hz, 1H), 6.91 (d, J=6.6 Hz, 1H), 4.56 (d, J=9.0 Hz, 1H), 4.13~3.96 (m, 1H), 3.68 (d, J=6.0 Hz, 2H), 2.85~2.65 (m, 2H), 1.86 (dd, J=12.4, 7.7 Hz, 1H), 1.68 (s, 1H), 1.42 (s, 9H). Ms (M$^+$+1): 320.

Example 41

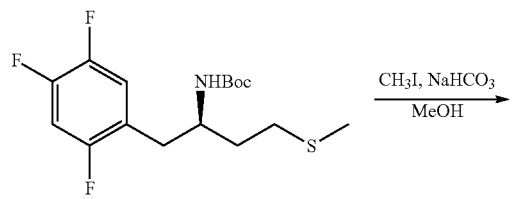

Into a three-necked flask was added a cold mixture of 35 ml distilled water and 5 ml methanol. The flask was placed in an ice-salt bath, and raw material as shown in the above reaction formula (4.29 g, 0.0123 mol) was added into the flask. 10 mL Iodomethane was withdrawn carefully with an injector and then added to the above reaction system. The reaction mixture was magnetically stirred for 30 min until the iodomethane at the bottom of the flask turned into colorless. The ice-salt bath was removed and the temperature of the reaction mixture was slowly increased to room temperature. The extent of reaction was assayed by TLC. After the reaction was completed and the reaction equipment was demounted, excess iodomethane volatilized in the air and the solvent was removed by distillation to obtain a crude product as a yellowish solid.

The obtained crude solid product was placed into a double-necked round-bottom flask and dissolved with 20 mL water. 10 mL Aqueous solution of 1.909 g (0.0227 mol) sodium hydrogen carbonate was added dropwise slowly to the above reaction mixture through a constant pressure dropping funnel, maintaining the pH of the reaction system 3-6. Then the reactants were heated slowly to reflux in an oil bath. The extent of reaction was detected by TLC. The pH value at the end point of the reaction was approximately 7. The solvent was removed by distillation to obtain a sticky and yellowish jelly. Dichloromethane (50 mL) and water (50 mL) were then added. After separation, the organic layer was washed with saturated solution of sodium hydrogen carbonate and dilute hydrochloric acid separately, and then dried over anhydrous sodium sulfate, followed by filtration and concentration to obtain a crude product (2.83 g, 72%).

$^1$H NMR (500 MHz, CDCl$_3$) δ 7.05 (d, J=8.3 Hz, 1H), 6.91 (d, J=6.6 Hz, 1H), 4.56 (d, J=9.0 Hz, 1H), 4.13~3.96 (m, 1H), 3.68 (d, J=6.0 Hz, 2H), 2.85~2.65 (m, 2H), 1.86 (dd, J=12.4, 7.7 Hz, 1H), 1.68 (s, 1H), 1.42 (s, 9H). Ms (M$^+$+1): 320.

Example 42

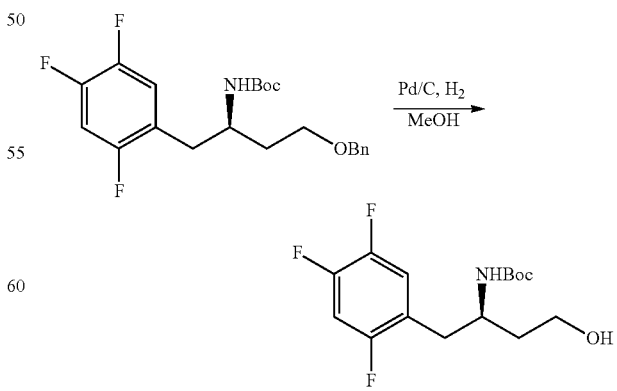

Raw material (5.41 g, 0.0132 mol) and 50 mL methanol and 0.5 g 10% Pd—C were added into a 250 mL autoclave and reacted under 6 atmospheres of hydrogen gas for 12 h. The catalyst was filtered out for recovery. Then the solvent was removed by distillation to obtain a crude product (4.13 g, 0.0129 mol). The yield was 98%.

$^1$H NMR (500 MHz, CDCl$_3$) δ 7.05 (d, J=8.3 Hz, 1H), 6.91 (d, J=6.6 Hz, 1H), 4.56 (d, J=9.0 Hz, 1H), 4.13~3.96 (m, 1H), 3.68 (d, J=6.0 Hz, 2H), 2.85~2.65 (m, 2H), 1.86 (dd, J=12.4, 7.7 Hz, 1H), 1.68 (s, 1H), 1.42 (s, 9H). Ms (M$^+$+1): 320.

Example 43

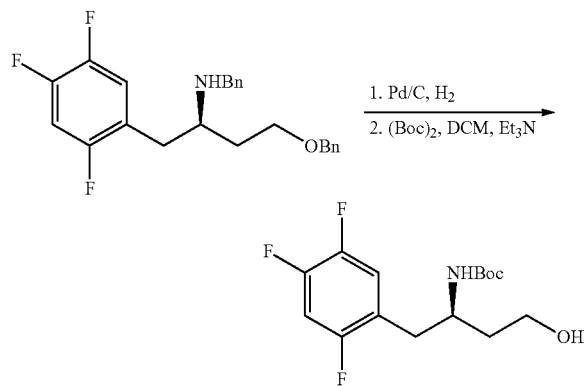

Raw material (5.11 g, 0.0128 mol) and 50 mL methanol and 0.5 g 20% Pd(OH)$_2$—C were added into a 250 mL autoclave and reacted under 6 atmospheres of hydrogen gas at 50° C. for 12 h. The catalyst was filtered out and recovered. Then the solvent was removed by distillation to obtain a crude product. Into a 100 mL round-bottom flask was added the crude product, 50 mL dichloromethane and triethylamine (2.6 g, 0.025 mol), followed by di-tert-butyl dicarbonate (3.27 g, 0.015 mol). After stirring for 8 h at room temperature, the mixture was washed with 50 mL dilute hydrochloric acid, followed by 50 mL water and finally 50 mL saturated solution of sodium hydrogen carbonate. The obtained was dried, filtered and concentrated to obtain a crude product (3.59 g, 0.011 mol). The total yield of the above two steps was 88%.

$^1$H NMR (500 MHz, CDCl$_3$) δ 7.05 (d, J=8.3 Hz, 1H), 6.91 (d, J=6.6 Hz, 1H), 4.56 (d, J=9.0 Hz, 1H), 4.13~3.96 (m, 1H), 3.68 (d, J=6.0 Hz, 2H), 2.85~2.65 (m, 2H), 1.86 (dd, J=12.4, 7.7 Hz, 1H), 1.68 (s, 1H), 1.42 (s, 9H). Ms (M$^+$+1): 320.

Example 44

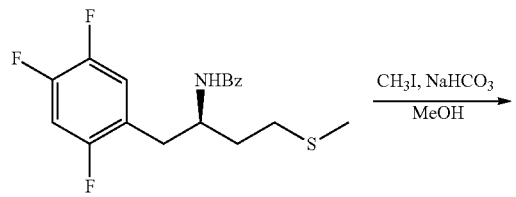

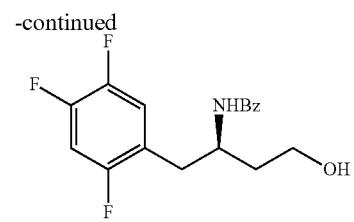

Into a three-necked flask was added a cold mixture of 35 ml distilled water and 5 ml methanol. The flask was placed in an ice-salt bath, and raw material (4.08 g, 0.0116 mol) was added into the flask. 10 mL Iodomethane was withdrawn carefully with an injector and then added to the above reaction system. The reaction mixture was magnetically stirred for 30 min until the iodomethane at the bottom of the flask turned into colorless. The ice-salt bath was removed and the temperature of the reaction mixture was increased to room temperature. The extent of reaction was assayed by TLC. After the reaction was completed and the reaction equipment was demounted, excess iodomethane volatilized in the air and the solvent was removed by distillation to obtain a crude product as a yellowish solid.

The obtained crude solid product was placed into a double-necked round-bottom flask and dissolved with 20 mL water. 10 mL Aqueous solution of 1.91 g (0.0227 mol) sodium hydrogen carbonate was added dropwise slowly to the above reaction mixture through a constant pressure dropping funnel, maintaining the pH of the reaction system 3-6. Then the reactants were heated slowly to reflux in an oil bath. The extent of reaction was detected by TLC. The pH value at the end point of the reaction was approximately 7. The solvent was removed by distillation to obtain a sticky and yellowish jelly. Dichloromethane (50 mL) and water (50 mL) were then added. After separation of the layers, the organic layer was washed with saturated solution of sodium hydrogen carbonate and dilute hydrochloric acid separately, and then dried over anhydrous sodium sulfate, followed by filtration and concentration to obtain a crude product (2.85 g, 77%).

$^1$H NMR (400 MHz, CDCl$_3$) δ 8.10 (d, J=5.4 Hz, 2H), 7.72~7.66 (m, 3H), 7.05 (d, J=8.3 Hz, 1H), 6.91 (d, J=6.6 Hz, 1H), 4.51 (d, J=9.0 Hz, 1H), 4.40 (br, 1H), 4.13~3.96 (m, 1H), 3.68 (d, J=6.0 Hz, 2H), 2.85~2.65 (m, 2H), 1.86 (dd, J=12.4, 7.7 Hz, 1H), 1.68 (s, 1H).

Example 45

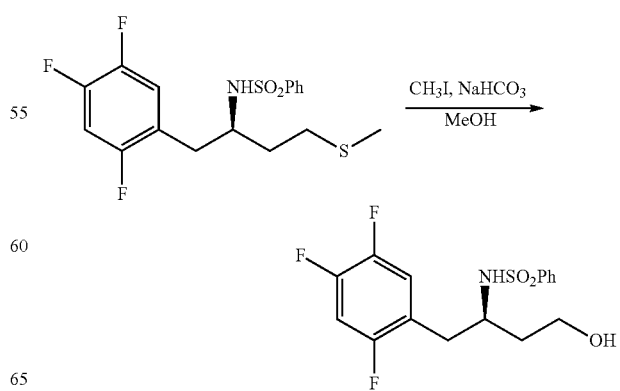

Into a three-necked flask was added a cold mixture of 35 ml distilled water and 5 ml methanol. The flask was placed in an ice-salt bath, and raw material (4.98 g, 0.0128 mol) was added into the flask. 10 mL Iodomethane was withdrawn carefully with an injector and then added to the above reaction system. The reaction mixture was magnetically stirred for 30 min until the iodomethane at the bottom of the flask turned into colorless. The ice-salt bath was removed and the temperature of the reaction mixture was increased to room temperature. The extent of reaction was assayed by TLC. After the reaction was completed and the reaction equipment was demounted, excess iodomethane volatilized in the air and the solvent was removed by distillation to obtain a crude product as a yellowish solid.

The obtained crude solid product was placed into a double-necked round-bottom flask and dissolved with 20 mL water. 10 mL Aqueous solution of 1.91 g (0.0227 mol) sodium hydrogen carbonate was added dropwise slowly to the above reaction mixture through a constant pressure dropping funnel, maintaining the pH of the reaction system 3-6. Then the reactants were heated slowly to reflux in an oil bath. The extent of reaction was detected by TLC. The pH value at the end point of the reaction was approximately 7. The solvent was removed by distillation to obtain a sticky and yellowish jelly. Dichloromethane (50 mL) and water (50 mL) were then added. After separation of the layers, the organic layer was washed with saturated solution of sodium hydrogen carbonate and dilute hydrochloric acid separately, and then dried over anhydrous sodium sulfate, followed by filtration and concentration to obtain a crude product (3.10 g, 76%).

$^1$H NMR (400 MHz, CDCl$_3$) δ 7.87~7.61 (m, 5H), 7.05 (d, J=8.3 Hz, 1H), 6.91 (d, J=6.6 Hz, 1H), 4.56 (d, J=9.0 Hz, 1H), 4.40 (br, 1H), 4.13~3.96 (m, 1H), 3.68 (d, J=6.0 Hz, 2H), 2.85~2.65 (m, 2H), 1.86 (dd, J=12.4, 7.7 Hz, 1H), 1.68 (s, 1H).

Example 46

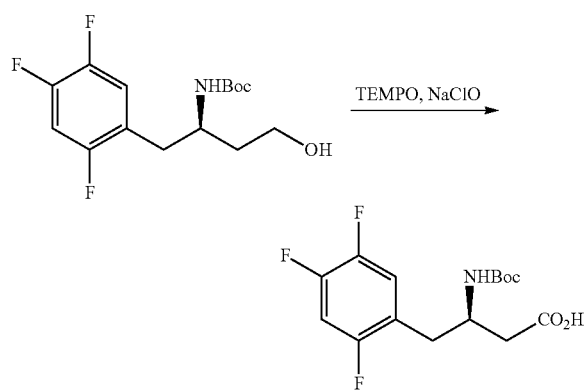

Into a three-necked flask equipped with constant-pressure dropping funnel and thermometer were added crude alcohol product (5.6 g, 0.0175 mol), 75 ml dichloromethane, 50 mL NaHCO$_3$ (5% solution), TEMPO (0.28 g, 1.75 mmol) and NaBr (0.18 g, 1.75 mmol). NaClO (50 mmol, 74 ml, 5%) was then added dropwise at 0° C. The reaction was completed after 2 h. To the obtained reaction mixture was added saturated 10 mL sodium thiosulfate and the pH of the reaction mixture was adjusted to 2-3 by neutralization with 2 N hydrochloric acid. After extracted with 50 mL dichloromethane three times, the obtained organic layers were collected together and further dried over anhydrous magnesium sulfate. The solvent was removed under a reduced pressure to obtain a solid crude product. Then, the obtained solid crude product was recrystallized from methanol to obtain an off-white solid (5.24 g, 0.0157 mol). The yield was 90%.

$^1$H NMR (500 MHz, CDCl$_3$) δ 7.09 (d, J=7.7 Hz, 1H), 6.91 (d, J=6.7 Hz, 1H), 5.03 (d, J=4.0 Hz, 1H), 4.36 (s, 1H), 3.06~2.75 (m, 3H), 2.62 (dd, J=16.4, 5.6 Hz, 1H), 2.50 (d, J=8.2 Hz, 1H), 1.33 (s, 9H). Ms (M$^+$+1): 334.

Example 47

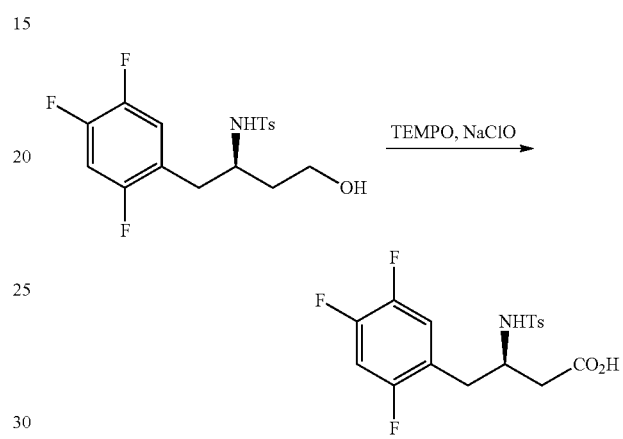

Into a three-necked flask equipped with constant-pressure dropping funnel and thermometer were added crude alcohol product (6.5 g, 0.0175 mol), 75 ml dichloromethane, 50 mL NaHCO$_3$ (5% solution), TEMPO (0.28 g, 1.75 mmol) and NaBr (0.18 g, 1.75 mmol). NaClO (50 mmol, 74 ml, 5%) was then added dropwise at 0° C. The reaction was completed after 2 h. To the obtained reaction mixture was added saturated 10 mL sodium thiosulfate and the pH of the reaction mixture was adjusted to 2-3 by neutralization with 2 N hydrochloric acid. After extracted with 50 mL dichloromethane three times, the obtained organic layers were collected together and further dried over anhydrous magnesium sulfate. The solvent was removed under a reduced pressure to obtain a solid crude product. Then, the obtained solid crude product was recrystallized from methanol to obtain 5.76 g off-white solid. The yield was 85%.

$^1$H NMR (400 MHz, CDCl$_3$) δ7.87~7.61 (m, 5H), 7.09 (d, J=7.7 Hz, 1H), 6.91 (d, J=6.7 Hz, 1H), 5.03 (d, J=4.0 Hz, 1H), 4.36 (s, 1H), 3.06~2.75 (m, 3H), 2.62 (dd, J=16.4, 5.6 Hz, 1H), 2.47 (d, J=8.2 Hz, 1H), 2.35 (s, 3H). Ms (M$^+$+1): 388.

Example 48

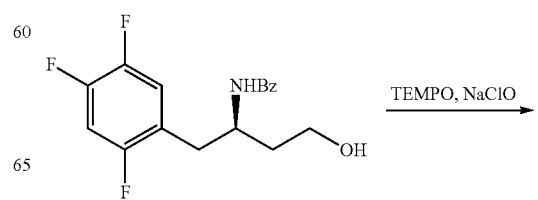

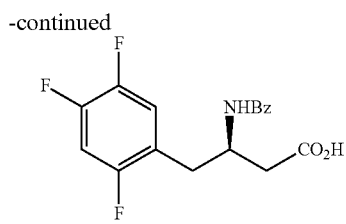

Into a three-necked flask equipped with constant-pressure dropping funnel and thermometer were added crude alcohol product (5.65 g, 0.0175 mol), 75 ml dichloromethane, 50 mL NaHCO$_3$ (5% solution), TEMPO (0.28 g, 1.75 mmol) and NaBr (0.18 g, 1.75 mmol). NaClO (50 mmol, 74 ml, 5%) was then added dropwise at 0° C. The reaction was completed after 2 h. To the obtained reaction mixture was added saturated 10 mL sodium thiosulfate and the pH of the reaction mixture was adjusted to 2-3 by neutralization with 2 N hydrochloric acid. After extracted with 50 mL dichloromethane three times, the obtained organic layers were collected together and further dried over anhydrous magnesium sulfate. The solvent was removed under a reduced pressure to obtain a solid crude product. Then, the obtained solid crude product was recrystallized from methanol to obtain an off-white solid (5.43 g, 0.0161 mol). The yield was 92%.

$^1$H NMR (400 MHz, CDCl$_3$) δ 8.10 (d, J=5.4 Hz, 2H), 7.72~7.66 (m, 3H), 7.09 (d, J=7.7 Hz, 1H), 6.91 (d, J=6.7 Hz, 1H), 5.03 (d, J=4.0 Hz, 1H), 4.36 (s, 1H), 3.06~2.75 (m, 3H), 2.62 (dd, J=16.4, 5.6 Hz, 1H), 2.50 (d, J=8.2 Hz, 1H). Ms (M$^+$+1): 338.

Example 49

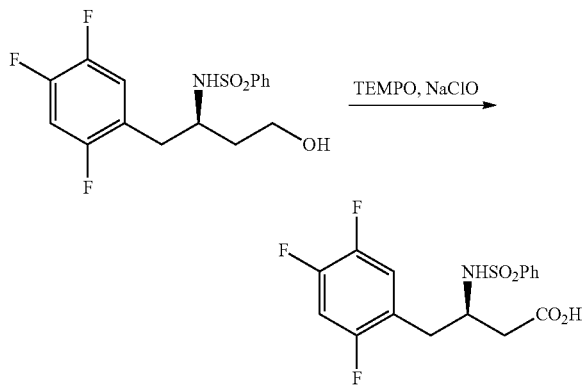

Into a three-necked flask equipped with constant-pressure dropping funnel and thermometer were added the crude alcohol product obtained in Example 45 (6.28 g, 0.0175 mol), dichloromethane (75 ml), NaHCO$_3$ (5% solution, 50 mL), TEMPO (0.28 g, 1.75 mmol) and NaBr (0.18 g, 1.75 mmol). NaClO (50 mmol, 74 ml, 5%) was then added dropwise at 0° C. The reaction was completed after 2 h. To the obtained reaction mixture was added saturated 10 mL sodium thiosulfate and the pH of the reaction mixture was adjusted to 2-3 by neutralization with 2 N hydrochloric acid. After extracted with 50 mL dichloromethane three times, the obtained organic layers were collected together and further dried over anhydrous magnesium sulfate. The solvent was removed under a reduced pressure to obtain a solid crude product. Then, the obtained solid crude product was recrystallized from methanol to obtain an off-white solid (5.74 g, 0.0154 mol). The yield was 88%.

$^1$H NMR (400 MHz, CDCl$_3$) δ7.87~7.61 (m, 5H), 7.09 (d, J=7.7 Hz, 1H), 6.91 (d, J=6.7 Hz, 1H), 5.03 (d, J=4.0 Hz, 1H), 4.36 (s, 1H), 3.06~2.75 (m, 3H), 2.62 (dd, J=16.4, 5.6 Hz, 1H), 2.47 (d, J=8.2 Hz, 1H). Ms (M$^+$+1): 374.

Example 50

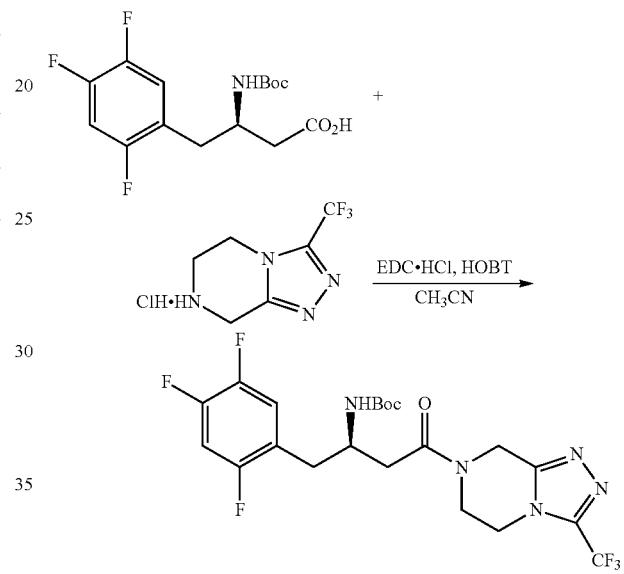

Into a 50 mL round-bottom flask was added 20 mL acetonitrile, followed by the addition of the phenyl-butyric acid derivative obtained in Example 46 (3.32 g, 0.01 mol) and triazolopyrazine hydrochloride (228 g, 0.01 mol). The temperature of the reaction mixture was cooled down to 0° C. in an ice-salt bath. 1-Hydroxylbenzotriazole (1.62 g, 0.012 mol) and 1-ethyl-3-(3-dimethylaminopropyl)carbodiimide hydrochloride (2.29 g, 0.012 mol) were further added. 3 g Triethylamine was then added dropwise and the mixture was stirred at room temperature for 24 h. The reaction solution was washed with 3×20 mL distilled water. The obtained organic layers were collected and dried over anhydrous magnesium sulfate for 1 h. Then, the desiccant was filtered off and the resulting reactant was concentrated to 4.81 g. The yield was 95%.

[α] D$^{20}$=+22.2 (c 1.0, CHCl$_3$). M.p. 188-191° C. IR (cm-1): 3374, 2897, 1686, 1635, 1519, 1368, 1164, 1128, 1016. $^1$H NMR (400 MHz, CDCl$_3$) δ 7.18~7.05 (m, 1H), 7.02-6.85 (m, 1H), 5.31 (s, 1H), 5.15~4.76 (m, 2H), 4.43~3.78 (m, 5H), 2.98~2.92 (m, 2H), 2.71~2.61 (m, 2H), 1.36 (s, 9H). ESI-MS: 508.0 (M++1). HRMS Calcd. for: C$_{21}$H$_{23}$F6N$_5$O$_3$Na (M+Na)+ requires 530.1598. found 530.1604.

Example 51

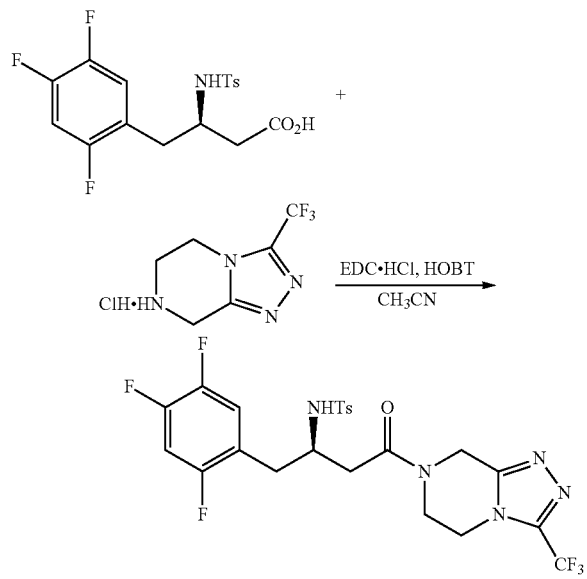

Into a 50 mL round-bottom flask was added 20 mL acetonitrile, followed by the addition of phenyl-butyric acid derivative (3.87 g, 0.01 mol) and triazolopyrazine hydrochloride (228 g, 0.01 mol). The temperature of the reaction mixture was cooled down to 0° C. in an ice-salt bath. 1-Hydroxylbenzotriazole (1.62 g, 0.012 mol) and 1-ethyl-3-(3-dimethylaminopropyl)carbodiimide hydrochloride (2.29 g, 0.012 mol) were further added. 3 g Triethylamine was then added dropwise and the mixture was stirred at room temperature for 24 h. The reaction solution was washed with 3×20 mL distilled water. The obtained organic layers were collected and dried over anhydrous magnesium sulfate for 1 h. Then, the desiccant was filtered off and the resulting reactant was concentrated to 5.1 g. The yield was 91%.

Example 52

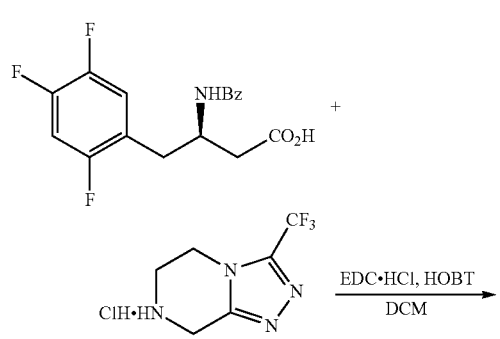

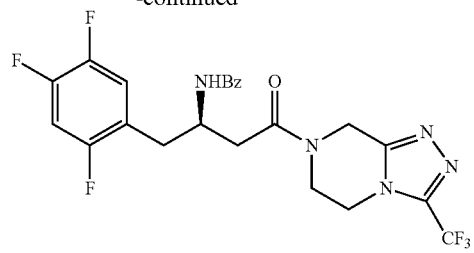

Into a 50 mL round-bottom flask was added 20 mL dichloromethane, followed by the addition of phenyl-butyric acid derivative (3.37 g, 0.01 mol) and triazolopyrazine hydrochloride (228 g, 0.01 mol). The temperature of the reaction mixture was cooled down to 0° C. in an ice-salt bath. 1-Hydroxylbenzotriazole (1.62 g, 0.012 mol) and 1-ethyl-3-(3-dimethylaminopropyl)carbodiimide hydrochloride (2.29 g, 0.012 mol) were further added. 3 g Triethylamine was then added dropwise and the mixture was stirred at room temperature for 24 h. The reaction solution was washed with 3×20 mL distilled water. The obtained organic layers were collected and dried over anhydrous magnesium sulfate for 1 h. Then, the desiccant was filtered off and the resulting reactant was concentrated to 4.7 g. The yield was 92%.

Example 53

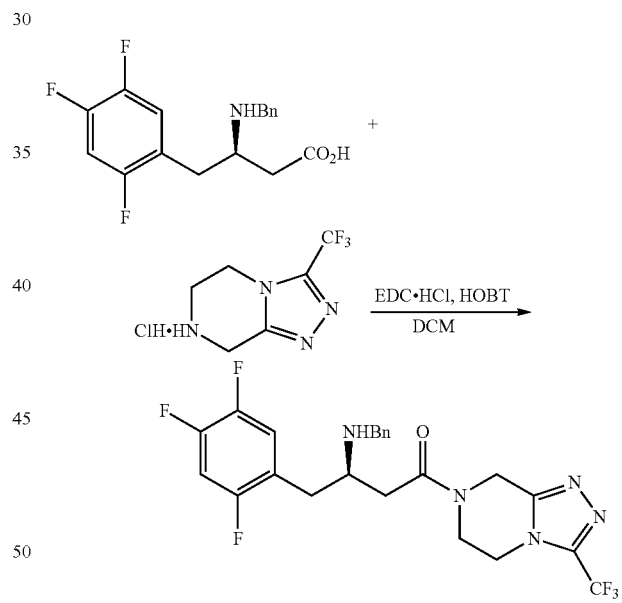

Into a 50 mL round-bottom flask was added 20 mL dichloromethane, followed by the addition of phenyl-butyric acid derivative (3.23 g, 0.01 mol) and triazolopyrazine hydrochloride (228 g, 0.01 mol). The temperature of the reaction mixture was cooled down to 0° C. in an ice-salt bath. 1-Hydroxylbenzotriazole (1.62 g, 0.012 mol) and 1-ethyl-3-(3-dimethylaminopropyl)carbodiimide hydrochloride (2.29 g, 0.012 mol) were further added. 3 g Triethylamine was then added dropwise and the mixture was stirred at room temperature for 24 h. The reaction solution was washed with 3×20 mL distilled water. The obtained organic layers were collected and dried over anhydrous magnesium sulfate for 1 h. Then, the desiccant was filtered off and the resulting reactant was concentrated to 4.67 g. The yield was 94%.

Example 54

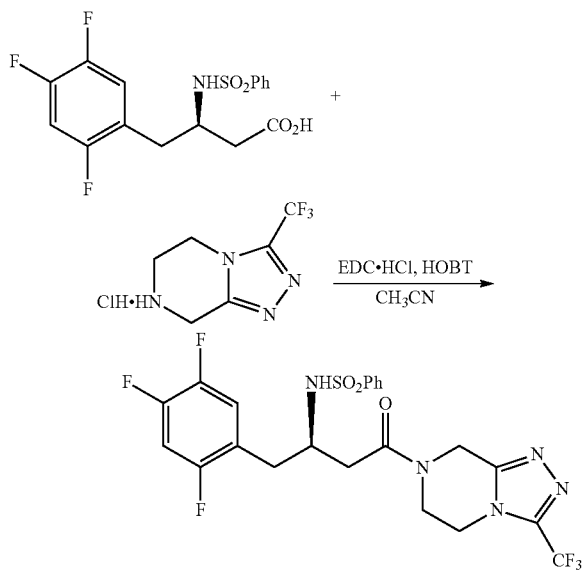

Into a 50 mL round-bottom flask was added 20 mL dichloromethane, followed by the addition of phenyl-butyric acid derivative (3.73 g, 0.01 mol) and triazolopyrazine hydrochloride (228 g, 0.01 mol). The temperature of the reaction mixture was cooled down to 0° C. in an ice-salt bath. 1-Hydroxy-1benzotriazole (1.62 g, 0.012 mol) and 1-ethyl-3-(3-dimethylaminopropyl)carbodiimide hydrochloride (2.29 g, 0.012 mol) were further added. 3 g Triethylamine was then added dropwise and the mixture was stirred at room temperature for 24 h. The reaction solution was washed with 3×20 mL distilled water. The obtained organic layers were collected and dried over anhydrous magnesium sulfate for 1 h. Then, the desiccant was filtered off and the resulting reactant was concentrated to 4.64 g. The yield was 85%.

Example 55

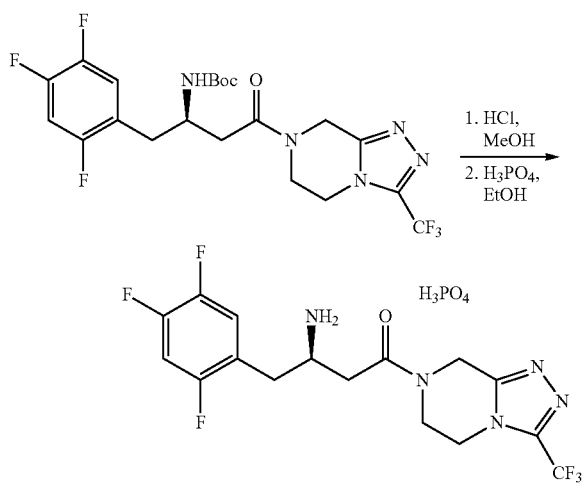

Into a 250 mL round-bottom flask were added raw material (5.07 g, 10 mmol), which was dissolved with addition of 50 mL methanol. 50 mL Solution of a mixture of concentrated hydrochloric acid and methanol with the ration of concentrated hydrochloric acid:methanol=1:5 (v/v) was added into the flask and stirred at room temperature for 2.5 h. TLC was used to monitor the progress of the reaction till the reaction was completed (pure ethyl acetate was applied on the plate, $R_f$ of the raw material=0.85, $R_f$ of the product=0.25). The solvent in the flask was concentrated to dryness by distillation and 2 mol/L ammonia solution was then added for neutralization. The aqueous layer was extracted with 3×100 mL ethyl acetate. The obtained organic layers were collected together and further washed with 200 mL saturated solution of sodium chloride and then dried over anhydrous magnesium sulfate for 1 h, followed by filtration and concentration to obtain a crude product as an oil.

Into the above crude product was added 60 mL anhydrous ethanol, followed by the addition of 10 mL water. The reaction mixture was heated to 80° C. and 1.5 g concentrated phosphoric acid was added. After reacting for 2 h under agitation, the reaction mixture was cooled down to room temperature and further stirred for 18 h. The solid was precipitated by filtration to obtain a phosphate of the crude product (4.39 g). The total yield of the above two steps was 87%.

$[\alpha]_D^{20}$=−22.8 (c 1.0, CHCl3). M.p. 108-112° C. IR (cm-1): 3360, 2870, 1644, 1517, 1437, 1342, 1237, 1140, 941, 808. $^1$H NMR (400 MHz, CDCl$_3$) δ7.19~7.02 (m, 1H), 7.02~6.81 (m, 1H) 5.06 (dd, J=50.1, 18.2 Hz, 1H), 4.95 (s, 2H), 4.43~3.77 (m, 5H), 3.60 (s, 1H), 2.92~2.28 (m, 4H). ESI-MS: 408.0 (M++1). HRMS Calcd. for: $C_{16}H_{15}F_6N_5ONa$ (M$^+$+Na)$^+$ requires 430.1082. found 430.1087.

Example 56

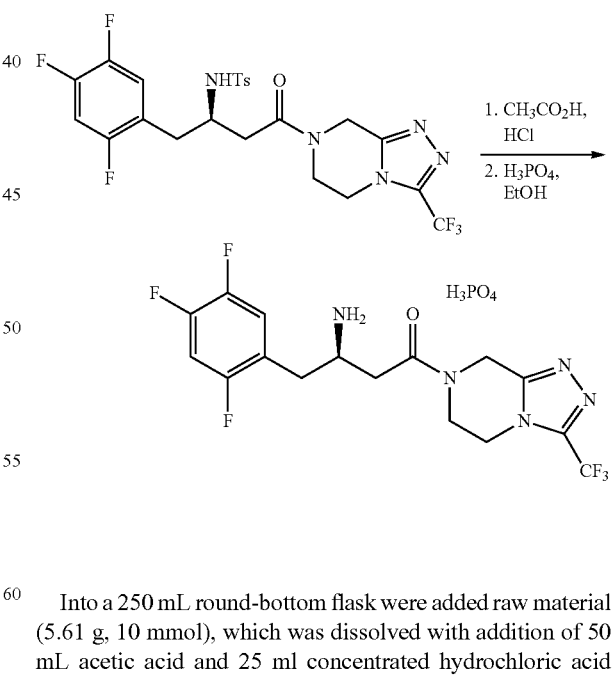

Into a 250 mL round-bottom flask were added raw material (5.61 g, 10 mmol), which was dissolved with addition of 50 mL acetic acid and 25 ml concentrated hydrochloric acid under agitation. The reaction mixture was heated gradually till it began to reflux. After stirring for 3 h, TLC was used to monitor the progress of the reaction till the reaction was completed. Then, the reaction mixture was poured into 200 g crushed ice and cooled down to room temperature. The pH of the reaction mixture was adjusted to 10 with the dissolution of 6N sodium hydroxide. The aqueous layer was extracted with 3×100 mL ethyl acetate. The organic layers were collected and washed by 200 mL saturated sodium chloride solution and dried over anhydrous magnesium sulfate for 1 h, followed by filtration and concentration to obtain a crude product as an oil.

Into the above crude product was added 60 mL anhydrous ethanol, followed by the addition of 10 mL water. The reaction mixture was heated to 80° C. and 1.5 g concentrated phosphoric acid was added. After reacting for 2 h under agitation, the reaction mixture was cooled down to room temperature and further stirred for 18 h. The solid was precipitated by filtration to obtain a phosphate of the crude product (3.25 g). The total yield of the above two steps was 65%.

Example 57

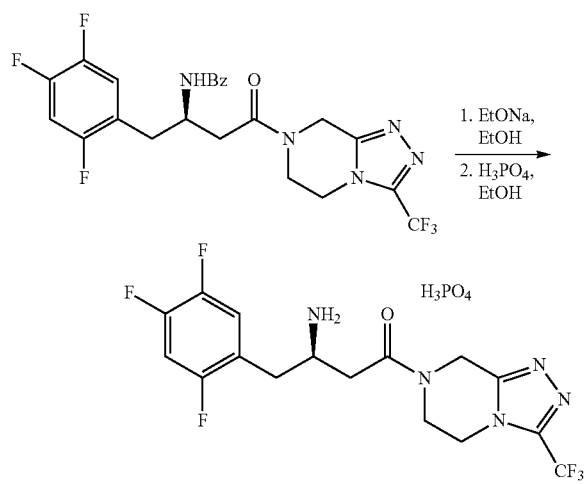

Into a 250 mL round-bottom flask were added raw material (5.11 g, 10 mmol), which was dissolved with addition of 50 mL methanol. Into the flask was added sodium ethoxide (3.4 g, 50 mmol) and stirred at room temperature for 7.5 h. TLC was used to monitor the progress of the reaction till the reaction was completed. The solvent was concentrated to dryness in the flask by distillation and 100 mL water was then added. The aqueous layer was extracted with 3×100 mL dichloromethane. The obtained organic layers were collected together and further washed with 200 mL saturated solution of sodium chloride and then dried over anhydrous magnesium sulfate for 1 h, followed by filtration and concentration to obtain a crude product as an oil.

Into the above crude product was added 60 mL anhydrous ethanol, followed by the addition of 10 mL water. The reaction mixture was heated to 80° C. and 1.5 g concentrated phosphoric acid was added. After reacting for 2 h under agitation, the reaction mixture was cooled down to room temperature and further stirred for 18 h. The solid was precipitated by filtration to obtain a phosphate of the crude product (3.78 g). The total yield of the above two steps was 75%.

Example 58

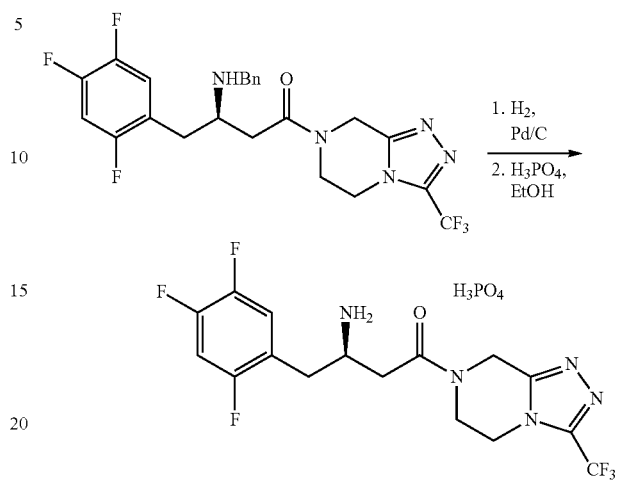

Into an autoclave were added raw material (4.97 g, 10 mmol), 10% Pd/C (0.5 g) and 120 mL methanol. The air in the autoclave was displaced with hydrogen gas three or four times. The reaction was stirred under 6 atm hydrogen gas at 45-50° C. for 10 h. After the reaction was completed, the catalyst was filtered out for recovery. The solvent was removed under a reduced pressure to obtain a solid crude product.

Into the above crude product was added 60 mL anhydrous ethanol, followed by the addition of 10 mL water. The reaction mixture was heated to 80° C. and 1.5 g concentrated phosphoric acid was added. After reacting for 2 h under agitation, the reaction mixture was cooled down to room temperature and further stirred for 18 h. The solid was precipitated by filtration to obtain a phosphate of the crude product (3.25 g). The total yield of the above two steps was 93%.

Example 59

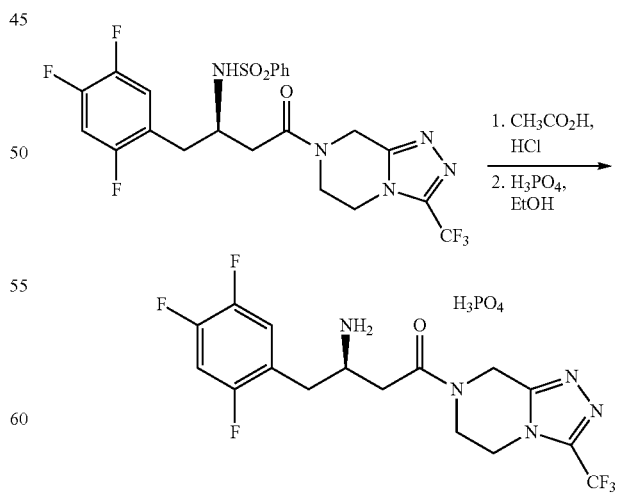

Into a 250 mL round-bottom flask were added raw material (5.47 g, 10 mmol), which was dissolved with addition of 50 mL acetic acid and 25 ml concentrated hydrochloric acid under agitation. The reaction mixture was heated gradually till it began to reflux. After stirring for 3 h, TLC was used to monitor the progress of the reaction till the reaction was completed. Then, the reaction mixture was poured into 200 g crushed ice and cooled down to room temperature. The pH of the reaction mixture was adjusted to 10 with the dissolution of 6N sodium hydroxide. The aqueous layer was extracted with 3×100 mL ethyl acetate. The organic layers were collected and washed by 200 mL saturated sodium chloride solution and dried over anhydrous magnesium sulfate for 1 h, followed by filtration and concentration to obtain a crude product as an oil.

Into the above crude product was added 60 mL anhydrous ethanol, followed by the addition of 10 mL water. The reaction mixture was heated to 80° C. and 1.5 g concentrated phosphoric acid was added. After reacting for 2 h under agitation, the reaction mixture was cooled down to room temperature and further stirred for 18 h. The solid was precipitated by filtration to obtain a phosphate of the crude product (3.5 g). The total yield of the above two steps was 70%.

The invention claimed is:

1. An aziridine compound (I) with absolute configuration R represented by Formula I:

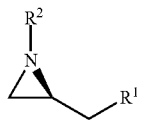

I wherein:
$R^1$ is —$CH_2SR^3$, wherein $R^3$ is $C_1$-$C_4$ alkyl; or $R^1$ is —$CH_2OR^4$, wherein $R^4$ is selected from the group consisting of methyl, substituted methyl, tetrahydropyranyl, methoxyphenyl, ethyl, benzyl, substituted benzyl and silyl;
wherein the substituted methyl is selected from the group consisting of methoxymethyl, methylthiomethyl, benzyloxymethyl, (p-methoxybenzyloxy)methyl, 2-methoxyethoxymethyl, and 2-trimethylsilylethoxymethyl;
the substituted benzyl is selected from the group consisting of p-methoxybenzyl, 3,4-dimethoxybenzyl and p-nitrobenzyl; and
the silyl is selected from the group consisting of trimethylsilyl, triethylsilyl, tri-isopropylsilyl, tert-butyldimethylsilyl, tert-butyldiphenylsilyl, diphenylmethylsilyl and tert-butylmethoxyphenylsilyl; and
$R^2$ is selected from the group consisting of hydrogen, formate group, acyl, sulfonyl, benzyl and 4-methoxybenzyl;
wherein the formate group is selected from the group consisting of methoxycarbonyl, ethoxycarbonyl, 9-fluorenylmethoxycarbonyl, 2-chloro-3-indenylmethoxycarbonyl, 2,2,2-trichloroethoxycarbonyl, 2-trimethylsilylethoxycarbonyl, homobenzyloxycarbonyl, tert-butoxycarbonyl, benzyloxycarbonyl and allyloxycarbonyl;
the acyl is selected from the group consisting of formyl, acetyl, trifluoroacetyl and benzoyl; and
the sulfonyl is trifluoromethylsulfonyl.

2. The aziridine compound (I) with absolute configuration R according to claim 1, wherein,
$R^1$ is —$CH_2SR^3$, wherein $R^3$ is methyl; or $R^1$ is —$CH_2OR^4$, wherein $R^4$ is selected from the group consisting of methoxymethyl, benzyl, p-nitrobenzyl, tert-butyldimethylsilyl and tert-butyldiphenylsilyl; and $R^2$ is selected from the group consisting of formate group, acyl, sulfonyl, benzyl and 4-methoxybenzyl, wherein the formate group is selected from the group consisting of methoxycarbonyl, tert-butoxycarbonyl, benzyloxycarbonyl and allyloxycarbonyl; the acyl is benzoyl; the sulfonyl is trifluoromethylsulfonyl.

3. The aziridine compound (I) with absolute configuration R according to claim 1, wherein, $R^1$ is —$CH_2SR^3$, wherein $R^3$ is methyl, or $R^1$ is —$CH_2OR^4$, wherein $R^4$ is selected from the group consisting of benzyl and tert-butyldimethylsilyl; and $R^2$ is selected from the group consisting of tert-butoxycarbonyl, and benzyl.

4. A process for synthesizing the aziridine compound (I) with absolute configuration R according to claim 1, wherein, the process comprises the step of intramolecular cyclizing an amino-compound (II) with absolute configuration R represented by Formula II

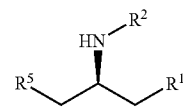

II in the presence of an alkali to form the aziridine compound (I) with absolute configuration R, wherein $R^1$ and $R^2$ are as defined in claim 1 and $R^5$ is selected from the group consisting of hydroxyl, sulfonate, and halogen; wherein the sulfonate is selected from the group consisting of methanesulfonate, p-toluenesulfonate, and trifluoromethanesulfonate; and the halogen is selected from the group consisting of chlorine, bromine, and iodine.

5. The process according to claim 4, wherein, $R^1$ is —$CH_2SR^3$, wherein $R^3$ is methyl, or $R^1$ is —$CH_2OR^4$, wherein $R^4$ is selected from the group consisting of benzyl and tert-butyldimethylsilyl; $R^2$ is selected from the group consisting of tert-butoxycarbonyl, and benzyl; $R^5$ is methanesulfonate or p-toluenesulfonate.

6. The process according to claim 4, wherein the alkali is organic alkali or inorganic alkali;
wherein the inorganic alkali is one or more alkalis selected from the group consisting of sodium hydroxide, potassium hydroxide, lithium hydride, sodium hydride, potassium hydride, calcium hydroxide, sodium carbonate, potassium phosphate and potassium carbonate;
the organic alkali is one or more alkalis selected from the group consisting of pyridine, substituted pyridine, piperidine, 1,8-diazabicyclo[5.4.0]undec-7-ene, $C_1$-$C_4$ aliphatic amine, $C_1$-$C_4$ sodium aliphatic alkoxide, $C_1$-$C_4$ potassium aliphatic alkoxide, butyl lithium, lithium diisopropylamide, lithium bis(trimethylsilyl)amide, sodlium bis(trimethylsilyl)amide and potassium bis(trimethylsilyl)amide.

7. The process according to claim 6, wherein the alkali is sodium hydride or sodium methoxide.

8. A process for synthesizing the chiral amino compound (IV) with configuration R, wherein, the process comprises a ring opening reaction of a metallic reagent of 2,4,5-trifluorobenzene (III)

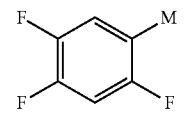

III with the aziridine compound (I) with absolute configuration R

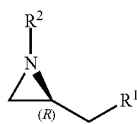

according to claim 1 to form a chiral amino acid compound (IV) with configuration R

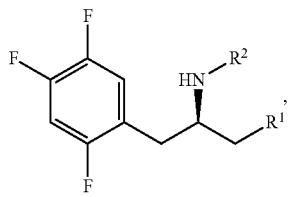

wherein M is selected from the group consisting of lithium, copper lithium, —Mg*Br, —Mg*Cl, and zinc.

9. The process according to claim 8, wherein, the metallic reagent of 2,4,5-trifluorobenzene (III) is 2,4,5-trifluorophenyl magnesium bromide.

10. A process for synthesizing Sitagliptin phosphate (X), wherein, the process comprises the following steps:

(1) performing a ring opening reaction of a metallic reagent of 2,4,5-trifluorobenzene (III)

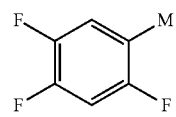

with the aziridine compound (I)

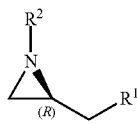

to form a chiral amino compound (IV) with configuration R

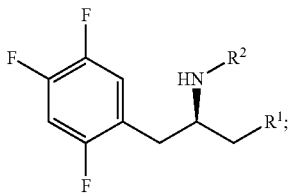

(2) preparing Sitagliptin phosphate (X)

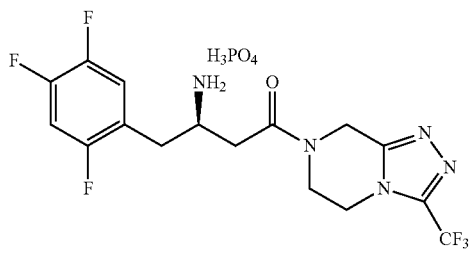

from the chiral amino-compound (IV)

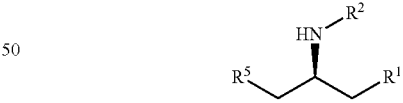

wherein:
$R^1$ is —$CH_2SR^3$, wherein $R^3$ is $C_1$-$C_4$ alkyl; or $R^1$ is —$CH_2OR^4$, wherein $R^4$ is selected from the group consisting of hydrogen, methyl, substituted methyl, tetrahydropyranyl, methoxyphenyl, ethyl, benzyl, substituted benzyl and silyl;
wherein the substituted methyl is selected from the group consisting of methoxymethyl, methylthiomethyl, benzyloxymethyl, (p-methoxybenzyloxy)methyl, 2-methoxyethoxymethyl, and 2-trimethylsilylethoxymethyl;
the substituted benzyl is selected from the group consisting of p-methoxybenzyl, 3,4-dimethoxybenzyl and p-nitrobenzyl;
the silyl is selected from the group consisting of trimethylsilyl, triethylsilyl, tri-isopropylsilyl, tert-butyldimethylsilyl, tert-butyldiphenylsilyl, diphenylmethylsilyl and tert-butylmethoxyphenylsilyl; and $R^2$ is selected from the group consisting of hydrogen, formate group, acyl, sulfonyl, and 4-methoxybenzyl;
wherein the formate group is selected from the group consisting of methoxycarbonyl, ethoxycarbonyl, 9-fluorenylmethoxycarbonyl, 2-chloro-3-indenylmethoxycarbonyl, 2,2,2-trichloroethoxycarbonyl, 2-trimethylsilylethoxycarbonyl, homobenzyloxycarbonyl, tert-butoxycarbonyl, benzyloxycarbonyl and allyloxycarbonyl;
the acyl is selected from the group consisting of formyl, acetyl, trifluoroacetyl and benzoyl;
the sulfonyl is benzenesulfonyl or trifluoromethylsulfonyl;
M is selected from the group consisting of lithium, copper lithium, —Mg.Br, —Mg.Cl and zinc.

11. The process according to claim 10, wherein, the process further comprises the following step prior to step (1):
intramolecular cyclizing an amino-compound (II) with absolute configuration R

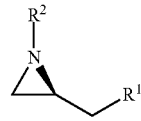

in the presence of an alkali to form a compound (I)

I

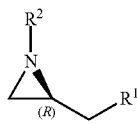

wherein $R^5$ is selected from the group consisting of hydroxyl, sulfonate and halogen, in which the sulfonate is selected from the group consisting of methanesulfonate, p-toluenesulfonate and trifluoromethanesulfonate; and the halogen is selected from the group consisting of chlorine, bromine and iodine.

12. The process according to claim 10, wherein, in step (2), when R1 in the amino compound (IV) is —CH$_2$OH, the chiral amino compound (IV) is beta-amino alcohol (V)

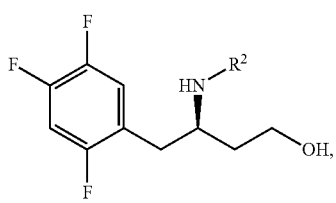
V which is firstly subjected to an oxidation reaction to form a beta-amino acid compound (VI)

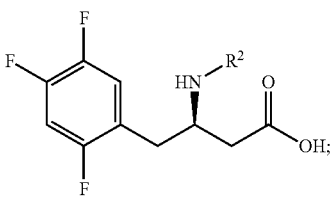
VI or, when R$^1$ in the amino compound (IV) is —CH$_2$SR$^3$, wherein R$^3$ is C$_1$-C$_4$ alkyl; or R$^1$ is —CH$_2$OR$^4$, wherein R$^4$ is selected from the group consisting of methyl, substituted methyl, tetrahydropyranyl, methoxyphenyl, ethyl, benzyl, substituted benzyl and silyl, wherein the substituted methyl is selected from the group consisting of methoxymethyl, methylthiomethyl, benzyloxymethyl, (p-methoxybenzyloxy)methyl, 2-methoxyethoxymethyl, and 2-trimethylsilylethoxymethyl; the substituted benzyl is selected from the group consisting of p-methoxybenzyl, 3,4-dimethoxybenzyl and p-nitrobenzyl; the silyl is selected from the group consisting of trimethylsilyl, triethylsilyl, tri-isopropylsilyl, tert-butyldimethylsilyl, tert-butyldiphenylsilyl, diphenylmethylsilyl and tert-butylmethoxyphenylsilyl, the sulphur alkyl or protective group on hydroxyl of the chiral amino compound (IV) with configuration R

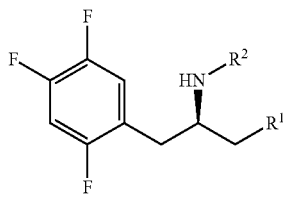
IV is firstly removed to form a chiral beta-amino alcohol (V)

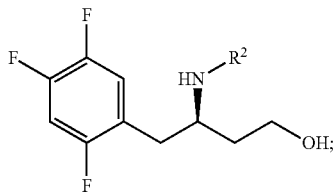
V then, the chiral beta-amino alcohol compound (V) is subjected to an oxidation reaction to form a beta-amino acid compound (VI)

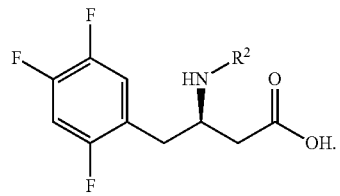
VI

13. The process according to claim 12, wherein, in step (2), the obtained beta-amino acid compound (VI)

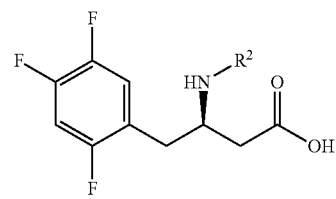
VI is subjected to a condensation reaction with a triazosin compound (VII)

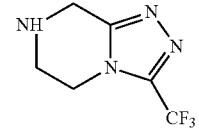
VII to form a Sitagliptin derivative (VIII)

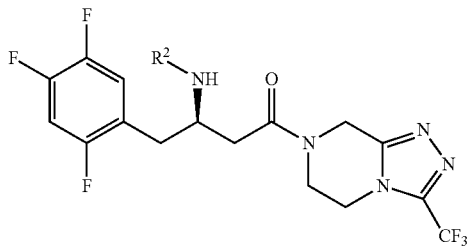
VIII having a protected amino-group.

14. The process according to claim 13, wherein, in step (2), the protective group R$^2$ is removed from the obtained Sitagliptin derivative (VIII)

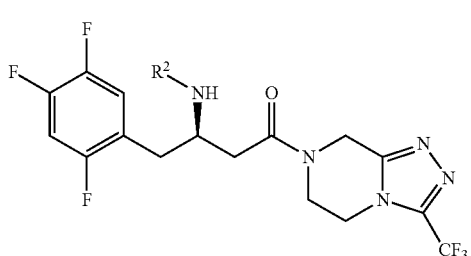
VIII to form Sitagliptin (IX)

IX

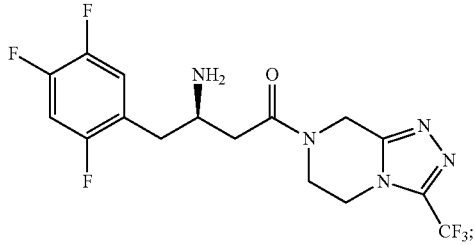

and the obtained Sitagliptin (IX) reacts with phosphoric acid to form Sitagliptin phosphate (X)

X

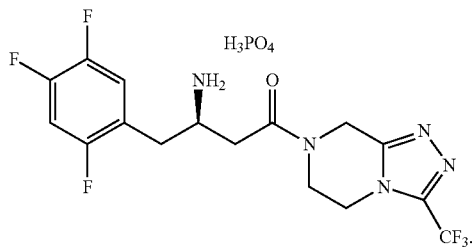

15. The process according to claim 5, wherein the alkali is organic alkali or inorganic alkali;
    wherein the inorganic alkali is one or more alkalis selected from the group consisting of sodium hydroxide, potassium hydroxide, lithium hydride, sodium hydride, potassium hydride, calcium hydroxide, sodium carbonate, potassium phosphate and potassium carbonate;
    the organic alkali is one or more alkalis selected from the group consisting of pyridine, substituted pyridine, piperidine, 1,8-diazabicyclo[5.4.0]undec-7-ene, $C_1$-$C_4$ aliphatic amine, $C_1$-$C_4$ sodium aliphatic alkoxide, $C_1$-$C_4$ potassium aliphatic alkoxide, butyl lithium, lithium diisopropylamide, lithium bis(trimethylsilyl)amide, sodlium bis(trimethylsilyl)amide and potassium bis(trimethylsilyl)amide.

16. The process according to claim 15, wherein the alkali is sodium hydride or sodium methoxide.

17. The process according to claim 11, wherein, in step (2), when $R^1$ in the amino compound (IV) is —$CH_2OH$, the chiral amino compound (IV) is beta-amino alcohol (V)

V

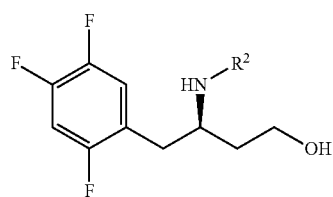

which is firstly subjected to an oxidation reaction to form a beta-amino acid compound (VI)

VI

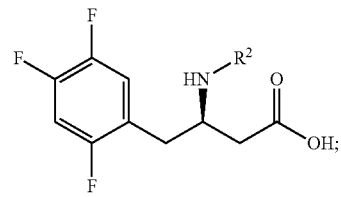

or,
when $R^1$ in the amino compound (IV) is —$CH_2SR^3$, wherein $R^3$ is $C_1$-$C_4$ alkyl; or $R^1$ is —$CH_2OR^4$, wherein $R^4$ is selected from the group consisting of methyl, substituted methyl, tetrahydropyranyl, methoxyphenyl, ethyl, benzyl, substituted benzyl and silyl, wherein the substituted methyl is selected from the group consisting of methoxymethyl, methylthiomethyl, benzyloxymethyl, (p-methoxybenzyloxy)methyl, 2-methoxyethoxymethyl, and 2-trimethylsilylethoxymethyl; the substituted benzyl is selected from the group consisting of p-methoxybenzyl, 3,4-dimethoxybenzyl and p-nitrobenzyl; the silyl is selected from the group consisting of trimethylsilyl, triethylsilyl, tri-isopropylsilyl, tert-butyldimethylsilyl, tert-butyldiphenylsilyl, diphenylmethylsilyl and tert-butylmethoxyphenylsilyl, the sulphur alkyl or protective group on hydroxyl of the chiral amino compound (IV) with configuration R

IV

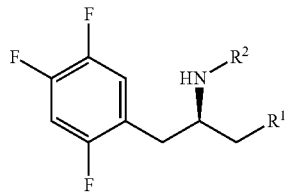

is firstly removed to form a chiral beta-amino alcohol (V); then, the chiral beta-amino alcohol compound (V)

V

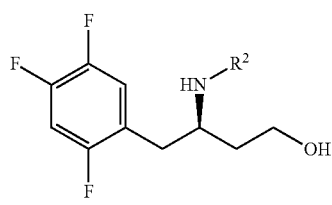

is subjected to an oxidation reaction to form a beta-amino acid compound (VI)

VI

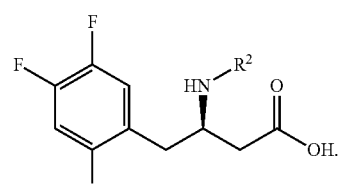

* * * * *